United States Patent
Park et al.

(10) Patent No.: US 9,655,053 B2
(45) Date of Patent: May 16, 2017

(54) WIRELESS PORTABLE ACTIVITY-MONITORING DEVICE SYNCING

(71) Applicant: Fitbit, Inc., San Francisco, CA (US)

(72) Inventors: James Park, Berkeley, CA (US); Heiko Gernot Albert Panther, Oakland, CA (US); Barry Christopher Burton, San Francisco, CA (US); Eric Nathan Friedman, San Francisco, CA (US)

(73) Assignee: FITBIT, INC., San Francisco, CA (US)

( * ) Notice: Subject to any disclaimer, the term of this patent is extended or adjusted under 35 U.S.C. 154(b) by 0 days.

(21) Appl. No.: 15/069,845

(22) Filed: Mar. 14, 2016

(65) Prior Publication Data

US 2016/0227484 A1    Aug. 4, 2016

Related U.S. Application Data

(63) Continuation of application No. 14/523,919, filed on Oct. 26, 2014, now Pat. No. 9,286,792, which is a
(Continued)

(51) Int. Cl.
*G06F 15/16*    (2006.01)
*H04W 52/02*    (2009.01)
(Continued)

(52) U.S. Cl.
CPC ....... *H04W 52/0254* (2013.01); *A61B 5/1118* (2013.01); *G08C 17/02* (2013.01);
(Continued)

(58) Field of Classification Search
USPC .................................................. 709/227
See application file for complete search history.

(56) References Cited

U.S. PATENT DOCUMENTS

| 2,717,736 A | 9/1955 | Schlesinger |
| 2,827,309 A | 3/1958 | Fred |

(Continued)

FOREIGN PATENT DOCUMENTS

| CN | 102111434 A | 6/2011 |
| CN | 102377815 A | 3/2012 |

(Continued)

OTHER PUBLICATIONS

Chandrasekar et al., "Plug-and-Play, Single-Chip Photoplethysmography", 34th Annual International Conference of the IEEE EMBS, San Diego, California USA, Aug. 28-Sep. 1, 2012, 4 pages.

(Continued)

*Primary Examiner* — Anthony Mejia
(74) *Attorney, Agent, or Firm* — Knobbe Martens Olson & Bear LLP

(57) ABSTRACT

A notification signal, intended to be received by a wireless communication device, is repetitively broadcast by a portable activity-monitoring device that generates user-activity data corresponding to activity of an individual bearing the portable activity-monitoring device. The notification signal conveys information that identifies the portable activity-monitoring device and indicates whether or not the portable activity-monitoring device seeks establishment of a wireless communication link to enable transmission of the user-activity data to the wireless communication device.

30 Claims, 22 Drawing Sheets

Related U.S. Application Data continuation of application No. 14/263,873, filed on Apr. 28, 2014, now Pat. No. 8,892,749, which is a continuation of application No. 14/047,852, filed on Oct. 7, 2013, now Pat. No. 8,745,247, which is a continuation of application No. 13/769,241, filed on Feb. 15, 2013, now Pat. No. 8,738,925.

(60) Provisional application No. 61/749,911, filed on Jan. 7, 2013.

(51) Int. Cl.

| | | |
|---|---|---|
| *H04K 1/00* | (2006.01) | |
| *G08C 17/02* | (2006.01) | |
| *H04B 7/26* | (2006.01) | |
| *H04L 12/18* | (2006.01) | |
| *H04Q 9/00* | (2006.01) | |
| *A61B 5/11* | (2006.01) | |
| *H04W 56/00* | (2009.01) | |
| *A61B 5/00* | (2006.01) | |

(52) U.S. Cl.
CPC .............. *H04B 7/26* (2013.01); *H04K 1/00* (2013.01); *H04L 12/189* (2013.01); *H04Q 9/00* (2013.01); *H04W 56/001* (2013.01); *A61B 5/0015* (2013.01); *H04Q 2209/43* (2013.01); *H04Q 2209/823* (2013.01)

(56) References Cited

U.S. PATENT DOCUMENTS

| | | |
|---|---|---|
| 2,883,255 A | 4/1959 | Anderson |
| 3,163,856 A | 12/1964 | Kirby |
| 3,250,270 A | 5/1966 | Walter |
| 3,522,383 A | 7/1970 | Chang |
| 3,918,658 A | 11/1975 | Beller |
| 4,192,000 A | 3/1980 | Lipsey |
| 4,244,020 A | 1/1981 | Ratcliff |
| 4,281,663 A | 8/1981 | Pringle |
| 4,284,849 A | 8/1981 | Anderson et al. |
| 4,312,358 A | 1/1982 | Barney |
| 4,367,752 A | 1/1983 | Jimenez et al. |
| 4,390,922 A | 6/1983 | Pelliccia |
| 4,407,295 A | 10/1983 | Steuer et al. |
| 4,425,921 A | 1/1984 | Fujisaki et al. |
| 4,575,804 A | 3/1986 | Ratcliff |
| 4,578,769 A | 3/1986 | Frederick |
| 4,617,525 A | 10/1986 | Lloyd |
| 4,887,249 A | 12/1989 | Thinesen |
| 4,930,518 A | 6/1990 | Hrushesky |
| 4,977,509 A | 12/1990 | Pitchford et al. |
| 5,058,427 A | 10/1991 | Brandt |
| 5,224,059 A | 6/1993 | Nitta et al. |
| 5,295,085 A | 3/1994 | Hoffacker |
| 5,314,389 A | 5/1994 | Dotan |
| 5,323,650 A | 6/1994 | Fullen et al. |
| 5,365,930 A | 11/1994 | Takashima et al. |
| 5,446,705 A | 8/1995 | Haas et al. |
| 5,456,648 A | 10/1995 | Edinburg et al. |
| 5,553,296 A | 9/1996 | Forrest et al. |
| 5,583,776 A | 12/1996 | Levi et al. |
| 5,645,509 A | 7/1997 | Brewer et al. |
| 5,671,162 A | 9/1997 | Werbin |
| 5,704,350 A | 1/1998 | Williams, III |
| 5,724,265 A | 3/1998 | Hutchings |
| 5,817,008 A | 10/1998 | Rafert et al. |
| 5,890,128 A | 3/1999 | Diaz et al. |
| 5,891,042 A | 4/1999 | Sham et al. |
| 5,894,454 A | 4/1999 | Kondo |
| 5,899,963 A | 5/1999 | Hutchings |
| 5,941,828 A | 8/1999 | Archibald et al. |
| 5,947,868 A | 9/1999 | Dugan |
| 5,955,667 A | 9/1999 | Fyfe |
| 5,976,083 A | 11/1999 | Richardson et al. |
| 6,018,705 A | 1/2000 | Gaudet et al. |
| 6,077,193 A | 6/2000 | Buhler et al. |
| 6,078,874 A | 6/2000 | Piety et al. |
| 6,085,248 A | 7/2000 | Sambamurthy et al. |
| 6,129,686 A | 10/2000 | Friedman |
| 6,145,389 A | 11/2000 | Ebeling et al. |
| 6,183,425 B1 | 2/2001 | Whalen et al. |
| 6,213,872 B1 | 4/2001 | Harada et al. |
| 6,241,684 B1 | 6/2001 | Amano et al. |
| 6,287,262 B1 | 9/2001 | Amano et al. |
| 6,301,964 B1 | 10/2001 | Fyfe et al. |
| 6,302,789 B2 | 10/2001 | Harada et al. |
| 6,305,221 B1 | 10/2001 | Hutchings |
| 6,309,360 B1 | 10/2001 | Mault |
| 6,469,639 B2 | 10/2002 | Tanenhaus et al. |
| 6,478,736 B1 | 11/2002 | Mault |
| 6,513,381 B2 | 2/2003 | Fyfe et al. |
| 6,513,532 B2 | 2/2003 | Mault et al. |
| 6,527,711 B1 | 3/2003 | Stivoric et al. |
| 6,529,827 B1 | 3/2003 | Beason et al. |
| 6,558,335 B1 | 5/2003 | Thede |
| 6,561,951 B2 | 5/2003 | Cannon et al. |
| 6,571,200 B1 | 5/2003 | Mault |
| 6,585,622 B1 | 7/2003 | Shum et al. |
| 6,607,493 B2 | 8/2003 | Song |
| 6,620,078 B2 | 9/2003 | Pfeffer |
| 6,678,629 B2 | 1/2004 | Tsuji |
| 6,699,188 B2 | 3/2004 | Wessel |
| 6,761,064 B2 | 7/2004 | Tsuji |
| 6,772,331 B1 | 8/2004 | Hind et al. |
| 6,790,178 B1 | 9/2004 | Mault et al. |
| 6,808,473 B2 | 10/2004 | Hisano et al. |
| 6,811,516 B1 | 11/2004 | Dugan |
| 6,813,582 B2 | 11/2004 | Levi et al. |
| 6,813,931 B2 | 11/2004 | Yadav et al. |
| 6,856,938 B2 | 2/2005 | Kurtz |
| 6,862,575 B1 | 3/2005 | Anttila et al. |
| 6,957,339 B2 | 10/2005 | Shinzaki |
| 7,041,032 B1 | 5/2006 | Calvano |
| 7,062,225 B2 | 6/2006 | White |
| 7,099,237 B2 * | 8/2006 | Lall .............. A61B 5/02438 368/10 |
| 7,133,690 B2 | 11/2006 | Ranta-Aho et al. |
| 7,162,368 B2 | 1/2007 | Levi et al. |
| 7,171,331 B2 | 1/2007 | Vock et al. |
| 7,200,517 B2 | 4/2007 | Darley et al. |
| 7,246,033 B1 | 7/2007 | Kudo |
| 7,261,690 B2 | 8/2007 | Teller et al. |
| 7,272,982 B2 | 9/2007 | Neuhauser et al. |
| 7,285,090 B2 | 10/2007 | Stivoric et al. |
| 7,373,820 B1 | 5/2008 | James |
| 7,443,292 B2 | 10/2008 | Jensen et al. |
| 7,457,724 B2 | 11/2008 | Vock et al. |
| 7,467,060 B2 | 12/2008 | Kulach et al. |
| 7,502,643 B2 | 3/2009 | Farringdon et al. |
| 7,505,865 B2 | 3/2009 | Ohkubo et al. |
| 7,539,532 B2 | 5/2009 | Tran |
| 7,558,622 B2 | 7/2009 | Tran |
| 7,559,877 B2 | 7/2009 | Parks et al. |
| 7,608,050 B2 | 10/2009 | Shugg |
| 7,653,508 B1 | 1/2010 | Kahn et al. |
| 7,690,556 B1 | 4/2010 | Kahn et al. |
| 7,713,173 B2 | 5/2010 | Shin et al. |
| 7,762,952 B2 | 7/2010 | Lee et al. |
| 7,771,320 B2 | 8/2010 | Riley et al. |
| 7,774,156 B2 | 8/2010 | Niva et al. |
| 7,789,802 B2 | 9/2010 | Lee et al. |
| 7,881,902 B1 | 2/2011 | Kahn et al. |
| 7,927,253 B2 | 4/2011 | Vincent et al. |
| 7,942,824 B1 | 5/2011 | Kayyali et al. |
| 7,953,549 B2 * | 5/2011 | Graham ............... G06Q 30/02 434/258 |
| 7,983,876 B2 | 7/2011 | Vock et al. |
| 8,005,922 B2 * | 8/2011 | Boudreau ............... H04W 4/08 709/217 |
| 8,028,443 B2 * | 10/2011 | Case, Jr. ............. A43B 1/0036 36/132 |
| 8,055,469 B2 | 11/2011 | Kulach et al. |

(56) References Cited

U.S. PATENT DOCUMENTS

| | | |
|---|---|---|
| 8,099,318 B2 | 1/2012 | Moukas et al. |
| 8,132,037 B2 | 3/2012 | Fehr et al. |
| 8,172,761 B1 | 5/2012 | Rulkov et al. |
| 8,177,260 B2 | 5/2012 | Tropper et al. |
| 8,180,591 B2 | 5/2012 | Yuen et al. |
| 8,180,592 B2 | 5/2012 | Yuen et al. |
| 8,270,297 B2 | 9/2012 | Akasaka et al. |
| 8,270,550 B2 * | 9/2012 | Horn .................. H04W 56/001 370/469 |
| 8,311,769 B2 | 11/2012 | Yuen et al. |
| 8,311,770 B2 | 11/2012 | Yuen et al. |
| 8,386,008 B2 | 2/2013 | Yuen et al. |
| 8,437,980 B2 | 5/2013 | Yuen et al. |
| 8,462,591 B1 | 6/2013 | Marhaben |
| 8,463,576 B2 | 6/2013 | Yuen et al. |
| 8,463,577 B2 | 6/2013 | Yuen et al. |
| 8,487,771 B2 | 7/2013 | Hsieh et al. |
| 8,533,269 B2 | 9/2013 | Brown |
| 8,533,620 B2 | 9/2013 | Hoffman et al. |
| 8,543,185 B2 | 9/2013 | Yuen et al. |
| 8,543,351 B2 | 9/2013 | Yuen et al. |
| 8,548,770 B2 | 10/2013 | Yuen et al. |
| 8,562,489 B2 | 10/2013 | Burton et al. |
| 8,583,402 B2 | 11/2013 | Yuen et al. |
| 8,597,093 B2 | 12/2013 | Engelberg et al. |
| 8,634,796 B2 | 1/2014 | Johnson |
| 8,638,228 B2 | 1/2014 | Amigo et al. |
| 8,670,953 B2 | 3/2014 | Yuen et al. |
| 8,684,900 B2 | 4/2014 | Tran |
| 8,690,578 B1 | 4/2014 | Nusbaum et al. |
| 8,738,321 B2 | 5/2014 | Yuen et al. |
| 8,738,323 B2 | 5/2014 | Yuen et al. |
| 8,738,925 B1 * | 5/2014 | Park ..................... H04B 7/26 380/270 |
| 8,744,803 B2 | 6/2014 | Park et al. |
| 8,762,101 B2 | 6/2014 | Yuen et al. |
| 8,764,651 B2 | 7/2014 | Tran |
| 8,847,988 B2 | 9/2014 | Geisner et al. |
| 8,868,377 B2 | 10/2014 | Yuen et al. |
| 8,949,070 B1 | 2/2015 | Kahn et al. |
| 8,954,290 B2 | 2/2015 | Yuen et al. |
| 8,961,414 B2 | 2/2015 | Teller et al. |
| 8,968,195 B2 | 3/2015 | Tran |
| 9,047,648 B1 | 6/2015 | Lekutai et al. |
| 2001/0049470 A1 | 12/2001 | Mault et al. |
| 2001/0055242 A1 | 12/2001 | Deshmuhk et al. |
| 2002/0013717 A1 | 1/2002 | Ando et al. |
| 2002/0019585 A1 | 2/2002 | Dickenson |
| 2002/0077219 A1 | 6/2002 | Cohen et al. |
| 2002/0082144 A1 | 6/2002 | Pfeffer |
| 2002/0087264 A1 | 7/2002 | Hills et al. |
| 2002/0109600 A1 | 8/2002 | Mault et al. |
| 2002/0178060 A1 | 11/2002 | Sheehan |
| 2002/0191797 A1 | 12/2002 | Perlman |
| 2002/0198776 A1 | 12/2002 | Nara et al. |
| 2003/0018523 A1 | 1/2003 | Rappaport et al. |
| 2003/0050537 A1 | 3/2003 | Wessel |
| 2003/0065561 A1 | 4/2003 | Brown et al. |
| 2003/0131059 A1 | 7/2003 | Brown et al. |
| 2003/0171189 A1 | 9/2003 | Kaufman |
| 2003/0226695 A1 | 12/2003 | Mault |
| 2004/0054497 A1 | 3/2004 | Kurtz |
| 2004/0061324 A1 | 4/2004 | Howard |
| 2004/0117963 A1 | 6/2004 | Schneider |
| 2004/0122488 A1 | 6/2004 | Mazar et al. |
| 2004/0152957 A1 | 8/2004 | Stivoric et al. |
| 2004/0239497 A1 | 12/2004 | Schwartzman et al. |
| 2004/0249299 A1 | 12/2004 | Cobb |
| 2004/0257557 A1 | 12/2004 | Block |
| 2005/0037787 A1 * | 2/2005 | Bachner, III ........ H04L 67/1095 455/502 |
| 2005/0037844 A1 | 2/2005 | Shum et al. |
| 2005/0038679 A1 | 2/2005 | Short |
| 2005/0054938 A1 | 3/2005 | Wehman et al. |
| 2005/0102172 A1 | 5/2005 | Sirmans, Jr. |
| 2005/0107723 A1 | 5/2005 | Wehman et al. |
| 2005/0163056 A1 | 7/2005 | Ranta-Aho et al. |
| 2005/0171410 A1 | 8/2005 | Hjelt et al. |
| 2005/0186965 A1 * | 8/2005 | Pagonis ............... G01S 5/0072 455/456.1 |
| 2005/0187481 A1 | 8/2005 | Hatib |
| 2005/0195830 A1 | 9/2005 | Chitrapu et al. |
| 2005/0216724 A1 | 9/2005 | Isozaki |
| 2005/0228244 A1 | 10/2005 | Banet |
| 2005/0228692 A1 | 10/2005 | Hodgdon |
| 2005/0234742 A1 | 10/2005 | Hodgdon |
| 2005/0248718 A1 | 11/2005 | Howell et al. |
| 2005/0272564 A1 | 12/2005 | Pyles et al. |
| 2006/0004265 A1 | 1/2006 | Pulkkinen et al. |
| 2006/0020174 A1 | 1/2006 | Matsumura |
| 2006/0020177 A1 | 1/2006 | Seo et al. |
| 2006/0025282 A1 | 2/2006 | Redmann |
| 2006/0039348 A1 | 2/2006 | Racz et al. |
| 2006/0047208 A1 | 3/2006 | Yoon |
| 2006/0047447 A1 | 3/2006 | Brady et al. |
| 2006/0064276 A1 | 3/2006 | Ren et al. |
| 2006/0069619 A1 | 3/2006 | Walker et al. |
| 2006/0069809 A1 * | 3/2006 | Serlet ................ G06F 17/30174 709/248 |
| 2006/0089542 A1 | 4/2006 | Sands |
| 2006/0111944 A1 | 5/2006 | Sirmans, Jr. |
| 2006/0129436 A1 | 6/2006 | Short |
| 2006/0143645 A1 | 6/2006 | Vock et al. |
| 2006/0166718 A1 | 7/2006 | Seshadri et al. |
| 2006/0217231 A1 | 9/2006 | Parks et al. |
| 2006/0247952 A1 | 11/2006 | Muraca |
| 2006/0277474 A1 | 12/2006 | Robarts et al. |
| 2006/0282021 A1 | 12/2006 | DeVaul et al. |
| 2006/0287883 A1 | 12/2006 | Turgiss et al. |
| 2006/0288117 A1 * | 12/2006 | Raveendran ............ H04L 12/66 709/236 |
| 2007/0011028 A1 * | 1/2007 | Sweeney ............... A61B 5/0031 705/3 |
| 2007/0049384 A1 | 3/2007 | King et al. |
| 2007/0050715 A1 | 3/2007 | Behar |
| 2007/0051369 A1 | 3/2007 | Choi et al. |
| 2007/0061593 A1 | 3/2007 | Celikkan et al. |
| 2007/0071643 A1 | 3/2007 | Hall et al. |
| 2007/0072156 A1 | 3/2007 | Kaufman et al. |
| 2007/0083095 A1 | 4/2007 | Rippo et al. |
| 2007/0083602 A1 | 4/2007 | Heggenhougen et al. |
| 2007/0123391 A1 | 5/2007 | Shin et al. |
| 2007/0135264 A1 | 6/2007 | Rosenberg |
| 2007/0136093 A1 | 6/2007 | Rankin et al. |
| 2007/0146116 A1 | 6/2007 | Kimbrell |
| 2007/0155277 A1 | 7/2007 | Amitai et al. |
| 2007/0159926 A1 | 7/2007 | Prstojevich et al. |
| 2007/0179356 A1 | 8/2007 | Wessel |
| 2007/0194066 A1 | 8/2007 | Ishihara et al. |
| 2007/0197920 A1 | 8/2007 | Adams |
| 2007/0208544 A1 | 9/2007 | Kulach et al. |
| 2007/0276271 A1 | 11/2007 | Chan |
| 2007/0288265 A1 | 12/2007 | Quinian et al. |
| 2008/0001735 A1 | 1/2008 | Tran |
| 2008/0014947 A1 * | 1/2008 | Carnall ................. G08B 21/22 455/437 |
| 2008/0022089 A1 | 1/2008 | Leedom |
| 2008/0032864 A1 | 2/2008 | Hakki |
| 2008/0044014 A1 | 2/2008 | Corndorf |
| 2008/0054072 A1 * | 3/2008 | Katragadda ........... G08G 1/123 235/384 |
| 2008/0084823 A1 | 4/2008 | Akasaka et al. |
| 2008/0093838 A1 | 4/2008 | Tropper et al. |
| 2008/0097550 A1 | 4/2008 | Dicks et al. |
| 2008/0114829 A1 | 5/2008 | Button et al. |
| 2008/0125288 A1 | 5/2008 | Case |
| 2008/0129457 A1 | 6/2008 | Ritter et al. |
| 2008/0134102 A1 | 6/2008 | Movold et al. |
| 2008/0140163 A1 | 6/2008 | Keacher et al. |
| 2008/0140338 A1 | 6/2008 | No et al. |
| 2008/0146892 A1 | 6/2008 | LeBoeuf et al. |
| 2008/0155077 A1 | 6/2008 | James |
| 2008/0176655 A1 | 7/2008 | James et al. |
| 2008/0275309 A1 | 11/2008 | Stivoric et al. |

(56) References Cited

U.S. PATENT DOCUMENTS

| | | |
|---|---|---|
| 2008/0287751 A1 | 11/2008 | Stivoric et al. |
| 2009/0018797 A1 | 1/2009 | Kasama et al. |
| 2009/0043531 A1 | 2/2009 | Kahn et al. |
| 2009/0047645 A1 | 2/2009 | Dibenedetto et al. |
| 2009/0048044 A1 | 2/2009 | Oleson et al. |
| 2009/0054737 A1 | 2/2009 | Magar et al. |
| 2009/0054751 A1* | 2/2009 | Babashan ............ A61B 5/0002 600/324 |
| 2009/0058635 A1 | 3/2009 | LaLonde et al. |
| 2009/0063193 A1 | 3/2009 | Barton et al. |
| 2009/0063293 A1 | 3/2009 | Mirrashidi et al. |
| 2009/0093341 A1* | 4/2009 | James ................ A63B 24/0062 482/1 |
| 2009/0098821 A1 | 4/2009 | Shinya |
| 2009/0144456 A1* | 6/2009 | Gelf .................... G06F 13/4022 710/8 |
| 2009/0144639 A1 | 6/2009 | Nims et al. |
| 2009/0150178 A1 | 6/2009 | Sutton et al. |
| 2009/0156172 A1 | 6/2009 | Chan |
| 2009/0171788 A1 | 7/2009 | Tropper et al. |
| 2009/0195350 A1 | 8/2009 | Tsern et al. |
| 2009/0262088 A1 | 10/2009 | Moll-Carrillo et al. |
| 2009/0264713 A1 | 10/2009 | Van Loenen et al. |
| 2009/0271147 A1 | 10/2009 | Sugai |
| 2009/0287921 A1 | 11/2009 | Zhu et al. |
| 2009/0307517 A1 | 12/2009 | Fehr et al. |
| 2009/0309742 A1 | 12/2009 | Alexander et al. |
| 2010/0023348 A1* | 1/2010 | Hardee ................ G06Q 10/00 705/3 |
| 2010/0058064 A1 | 3/2010 | Kirovski et al. |
| 2010/0059561 A1 | 3/2010 | Ellis et al. |
| 2010/0069203 A1 | 3/2010 | Kawaguchi et al. |
| 2010/0125729 A1 | 5/2010 | Baentsch et al. |
| 2010/0130873 A1 | 5/2010 | Yuen et al. |
| 2010/0158494 A1* | 6/2010 | King .................... G03B 17/00 396/56 |
| 2010/0159709 A1 | 6/2010 | Kotani et al. |
| 2010/0167783 A1 | 7/2010 | Alameh et al. |
| 2010/0179411 A1* | 7/2010 | Holmstrom .......... A61B 5/0464 600/374 |
| 2010/0185064 A1 | 7/2010 | Bandic et al. |
| 2010/0205541 A1 | 8/2010 | Rapaport et al. |
| 2010/0217099 A1 | 8/2010 | LeBoeuf et al. |
| 2010/0222179 A1* | 9/2010 | Temple ............... A63B 24/0062 482/8 |
| 2010/0261987 A1 | 10/2010 | Kamath et al. |
| 2010/0292050 A1 | 11/2010 | DiBenedetto |
| 2010/0292600 A1* | 11/2010 | DiBenedetto ...... A63B 24/0062 600/520 |
| 2010/0295684 A1* | 11/2010 | Hsieh ................... A61B 5/1118 340/573.1 |
| 2010/0298661 A1 | 11/2010 | McCombie et al. |
| 2010/0304674 A1 | 12/2010 | Kim et al. |
| 2010/0311544 A1* | 12/2010 | Robinette ............. A63B 24/00 482/8 |
| 2010/0331145 A1 | 12/2010 | Lakovic et al. |
| 2011/0003665 A1 | 1/2011 | Burton et al. |
| 2011/0009051 A1 | 1/2011 | Khedouri et al. |
| 2011/0021143 A1 | 1/2011 | Kapur et al. |
| 2011/0022349 A1 | 1/2011 | Stirling et al. |
| 2011/0080349 A1 | 4/2011 | Holbein et al. |
| 2011/0087076 A1 | 4/2011 | Brynelsen et al. |
| 2011/0106449 A1 | 5/2011 | Chowdhary et al. |
| 2011/0131005 A1 | 6/2011 | Ueshima et al. |
| 2011/0145894 A1 | 6/2011 | Garcia Morchon et al. |
| 2011/0153773 A1* | 6/2011 | Vandwalle ............ H04W 8/005 709/217 |
| 2011/0167262 A1 | 7/2011 | Ross et al. |
| 2011/0193704 A1 | 8/2011 | Harper et al. |
| 2011/0197157 A1 | 8/2011 | Hoffman et al. |
| 2011/0214030 A1 | 9/2011 | Greenberg et al. |
| 2011/0221590 A1 | 9/2011 | Baker et al. |
| 2011/0224508 A1 | 9/2011 | Moon |
| 2011/0230729 A1 | 9/2011 | Shirasaki et al. |
| 2011/0258689 A1 | 10/2011 | Cohen et al. |
| 2012/0035487 A1* | 2/2012 | Werner ............... A63B 24/0062 600/508 |
| 2012/0072165 A1 | 3/2012 | Jallon |
| 2012/0083705 A1 | 4/2012 | Yuen et al. |
| 2012/0083714 A1 | 4/2012 | Yuen et al. |
| 2012/0083715 A1 | 4/2012 | Yuen et al. |
| 2012/0083716 A1 | 4/2012 | Yuen et al. |
| 2012/0084053 A1 | 4/2012 | Yuen et al. |
| 2012/0084054 A1 | 4/2012 | Yuen et al. |
| 2012/0092157 A1 | 4/2012 | Tran |
| 2012/0094649 A1 | 4/2012 | Porrati et al. |
| 2012/0102008 A1 | 4/2012 | Kääriäinen et al. |
| 2012/0116684 A1 | 5/2012 | Ingrassia, Jr. et al. |
| 2012/0119911 A1 | 5/2012 | Jeon et al. |
| 2012/0165684 A1 | 6/2012 | Sholder |
| 2012/0166257 A1 | 6/2012 | Shiragami et al. |
| 2012/0179278 A1 | 7/2012 | Riley et al. |
| 2012/0183939 A1 | 7/2012 | Aragones et al. |
| 2012/0215328 A1* | 8/2012 | Schmelzer .......... G06F 19/3481 700/91 |
| 2012/0226471 A1 | 9/2012 | Yuen et al. |
| 2012/0226472 A1 | 9/2012 | Yuen et al. |
| 2012/0227737 A1 | 9/2012 | Mastrototaro et al. |
| 2012/0265480 A1 | 10/2012 | Oshima |
| 2012/0274508 A1* | 11/2012 | Brown ................... G04F 10/00 342/357.25 |
| 2012/0283855 A1 | 11/2012 | Hoffman et al. |
| 2012/0290109 A1 | 11/2012 | Engelberg et al. |
| 2012/0296400 A1 | 11/2012 | Bierman et al. |
| 2012/0297229 A1* | 11/2012 | Desai .................. H04W 76/023 713/340 |
| 2012/0316456 A1 | 12/2012 | Rahman et al. |
| 2012/0324226 A1 | 12/2012 | Bichsel et al. |
| 2012/0330109 A1 | 12/2012 | Tran |
| 2013/0006718 A1 | 1/2013 | Nielsen et al. |
| 2013/0041590 A1 | 2/2013 | Burich et al. |
| 2013/0072169 A1 | 3/2013 | Ross et al. |
| 2013/0073254 A1 | 3/2013 | Yuen et al. |
| 2013/0073255 A1 | 3/2013 | Yuen et al. |
| 2013/0080113 A1 | 3/2013 | Yuen et al. |
| 2013/0094600 A1 | 4/2013 | Beziat et al. |
| 2013/0095459 A1 | 4/2013 | Tran |
| 2013/0096843 A1 | 4/2013 | Yuen et al. |
| 2013/0102251 A1 | 4/2013 | Linde et al. |
| 2013/0103847 A1 | 4/2013 | Brown et al. |
| 2013/0106684 A1* | 5/2013 | Weast ................. G06F 19/3481 345/156 |
| 2013/0132501 A1* | 5/2013 | Vandwalle ............ H04L 67/104 709/208 |
| 2013/0151196 A1 | 6/2013 | Yuen et al. |
| 2013/0158369 A1 | 6/2013 | Yuen et al. |
| 2013/0166048 A1* | 6/2013 | Werner ................ H04L 67/18 700/91 |
| 2013/0190008 A1 | 7/2013 | Vathsangam et al. |
| 2013/0190903 A1 | 7/2013 | Balakrishnan et al. |
| 2013/0191034 A1 | 7/2013 | Weast et al. |
| 2013/0203475 A1* | 8/2013 | Kil ........................ A63F 13/00 463/7 |
| 2013/0209972 A1* | 8/2013 | Carter ................ G09B 19/0092 434/127 |
| 2013/0225117 A1* | 8/2013 | Giacoletto ............ H04W 4/22 455/404.2 |
| 2013/0228063 A1 | 9/2013 | Turner |
| 2013/0231574 A1 | 9/2013 | Tran |
| 2013/0238287 A1 | 9/2013 | Hoffman et al. |
| 2013/0261475 A1 | 10/2013 | Mochizuki |
| 2013/0267249 A1 | 10/2013 | Rosenberg |
| 2013/0268199 A1* | 10/2013 | Nielsen ................ B65D 83/203 702/7 |
| 2013/0268236 A1 | 10/2013 | Yuen et al. |
| 2013/0268687 A1 | 10/2013 | Schrecker |
| 2013/0268767 A1 | 10/2013 | Schrecker |
| 2013/0274904 A1 | 10/2013 | Coza et al. |
| 2013/0281110 A1* | 10/2013 | Zelinka ................. G01S 5/0284 455/456.1 |
| 2013/0289366 A1 | 10/2013 | Chua et al. |
| 2013/0296666 A1 | 11/2013 | Kumar et al. |

(56) References Cited

U.S. PATENT DOCUMENTS

| | | | |
|---|---|---|---|
| 2013/0296672 A1 | 11/2013 | O'Neil et al. | |
| 2013/0296673 A1 | 11/2013 | Thaveeprungsriporn et al. | |
| 2013/0310896 A1 | 11/2013 | Mass | |
| 2013/0325396 A1 | 12/2013 | Yuen et al. | |
| 2013/0331058 A1* | 12/2013 | Harvey | H04W 4/22 455/404.2 |
| 2013/0337974 A1 | 12/2013 | Yanev et al. | |
| 2013/0345978 A1 | 12/2013 | Lush et al. | |
| 2014/0035761 A1 | 2/2014 | Burton et al. | |
| 2014/0039804 A1 | 2/2014 | Park et al. | |
| 2014/0039840 A1 | 2/2014 | Yuen et al. | |
| 2014/0039841 A1 | 2/2014 | Yuen et al. | |
| 2014/0052280 A1 | 2/2014 | Yuen et al. | |
| 2014/0067278 A1 | 3/2014 | Yuen et al. | |
| 2014/0077673 A1 | 3/2014 | Garg et al. | |
| 2014/0085077 A1* | 3/2014 | Luna | G08B 6/00 340/539.11 |
| 2014/0085136 A1* | 3/2014 | Alpert | H04W 56/005 342/357.25 |
| 2014/0094941 A1 | 4/2014 | Ellis et al. | |
| 2014/0125618 A1 | 5/2014 | Panther et al. | |
| 2014/0164611 A1 | 6/2014 | Molettiere et al. | |
| 2014/0180022 A1 | 6/2014 | Stivoric et al. | |
| 2014/0200691 A1 | 7/2014 | Lee et al. | |
| 2014/0207264 A1 | 7/2014 | Quy | |
| 2014/0213858 A1 | 7/2014 | Presura et al. | |
| 2014/0275885 A1 | 9/2014 | Isaacson et al. | |
| 2014/0278229 A1 | 9/2014 | Hong et al. | |
| 2014/0316305 A1 | 10/2014 | Venkatraman et al. | |
| 2014/0337451 A1 | 11/2014 | Choudhary et al. | |
| 2014/0337621 A1 | 11/2014 | Nakhimov | |
| 2015/0026647 A1 | 1/2015 | Park et al. | |
| 2015/0374267 A1 | 12/2015 | Laughlin | |
| 2016/0063888 A1 | 3/2016 | McCallum et al. | |
| 2016/0089572 A1 | 3/2016 | Liu et al. | |
| 2016/0107646 A1 | 4/2016 | Kolisetty et al. | |

FOREIGN PATENT DOCUMENTS

| | | | |
|---|---|---|---|
| CN | 103226647 | 7/2013 | |
| JP | 11347021 A | 12/1999 | |
| RU | 2178588 C1 | 1/2002 | |
| WO | WO 0211019 A1 | 2/2002 | |
| WO | WO 2006055125 A1 | 5/2006 | |
| WO | WO 2006090197 A1 | 8/2006 | |
| WO | WO 2008038141 A2 | 4/2008 | |
| WO | WO 2009042965 A1 | 4/2009 | |
| WO | WO 2012061438 A2 * | 5/2012 | A61B 5/681 |
| WO | WO 2012/170586 | 12/2012 | |
| WO | WO 2012/170924 | 12/2012 | |
| WO | WO 2012/171032 | 12/2012 | |
| WO | WO 2015/127067 | 8/2015 | |
| WO | WO 2016/003269 | 1/2016 | |

OTHER PUBLICATIONS

Clifford et al., "Altimeter and Barometer System", Freescale Semiconductor Application Note AN1979, Rev. 3, Nov. 2006, 10 pages.
Fang et al, "Design of a Wireless Assisted Pedestrian Dead Reckoning System—The NavMote Experience", IEEE Transactions on Instrumentation and Measurement, vol. 54, No. 6, Dec. 2005, pp. 2342-2358.
Fitbit Inc., "Fitbit Automatically Tracks Your Fitness and Sleep" published online at web.archive.org/web/20080910224820/http://www.fitbit.com, copyright Sep. 10, 2008, 1 page.
Godfrey et al., "Direct Measurement of Human Movement by Accelerometry", Medical Engineering & Physics, vol. 30, 2008, pp. 1364-1386 (22 pages).
Godha et al., "Foot Mounted Inertia System for Pedestrian Naviation", Measurement Science and Technology, vol. 19, No. 7, May 2008, pp. 1-9 (10 pages).
Intersema, "Using MS5534 for altimeters and barometers", Application Note AN501, Jan. 2006, 12pages.
Ladetto et al, "On Foot Navigation: When GPS alone is not Enough", Journal of Navigation, vol. 53, No. 2, Sep. 2000, pp. 279-285 (6 pages).
Lammel et al., "Indoor Navigation with MEMS Sensors", Proceedings of the Eurosensors XIII conference, vol. 1, No. 1, Sep. 2009, pp. 532-535 (4 pages).
Lester et al, "Validated caloric expenditure estimation using a single body-worn sensor", Proc. of the Int'l Conf. on Ubiquitous Computing, 2009, pp. 225-234 (10 pages).
Lester et al., "A Hybrid Discriminative/Generative Approach for Modeling Human Activities", Proc. of the Int'l Joint Conf. Artificial Intelligence, 2005, pp. 766-772 (7 pages).
Ohtaki et al, "Automatic classification of ambulatory movements and evaluation of energy consumptions utilizing accelerometers and barometer", Microsystem Technologies, vol. 11, No. 8-10, Aug. 2005, pp. 1034-1040 (7 pages).
Parkka, et al, Activity Classification Using Realistic Data From Wearable Sensors, IEEE Transactions on Information Technology in Biomedicine, vol. 10, No. 1, Jan. 2006, pp. 119-128 (10pages).
PCT/IB07/03617 International Search Report issued on Aug. 15, 2008, 3 pages.
Perrin et al, "Improvement of Walking Speed Prediction by Accelerometry and Altimetry, Validated by Satellite Positioning", Medical & Biological Engineering & Computing, vol. 38, 2000, pp. 164-168 (5 pages).
Retscher, "An Intelligent Multi-Sensor system for Pedestrian Navigation", Journal of Global Positioning Systems, vol. 5, No. 1, 2006, pp. 110-118 (9 pages).
Sagawa et al, "Classification of Human Moving Patterns Using Air Pressure and Acceleration", Proceedings of the 24th Annual Conference of the IEEE Industrial Electronics Society, vol. 2, Aug.-Sep. 1998, pp. 1214-1219 (6 pages).
Sagawa et al, "Non-restricted measurement of walking distance", IEEE Int'l Conf. on Systems, Man, and Cybernetics, vol. 3, Oct. 2000, pp. 1847-1852 (6 pages).
Specification of the Bluetooth® System, Core Package, version 4.1, Dec. 2013, vols. 0 & 1, 282 pages.
Stirling et al., "Evaluation of a New Method of Heading Estimation of Pedestrian Dead Reckoning Using Shoe Mounted Sensors", Journal of Navigation, vol. 58, 2005, pp. 31-45 (15 pages).
Suunto Lumi, "User Guide", Copyright Jun. and Sep. 2007, 49 pages.
Tanigawa et al, "Drift-Free Dynamic Height Sensor Using MEMS IMU Aided by MEMS Pressure Sensor", Workshop on Positioning, Navigation and Communication, Mar. 2008, pp. 191-196 (6 pages).
VTI Technologies, "SCP 1000-D01/D11 Pressure Sensor as Barometer and Altimeter", Application Note 33, Jun. 2006, 3 pages.

* cited by examiner

WIRELESS PORTABLE ACTIVITY-MONITORING DEVICE SYNCING

CLAIM OF PRIORITY

This application is a continuation application of U.S. patent application Ser. No. 14/523,919, filed on Oct. 26, 2014, and entitled "Wireless Portable Activity-Monitoring Device Syncing," which is a continuation of U.S. patent application Ser. No. 14/263,873 filed Apr. 28, 2014 and entitled "Wireless Portable Activity-Monitoring Device Syncing," which is a continuation of U.S. patent application Ser. No. 14/047,852 filed Oct. 7, 2013 and entitled "Wireless Portable Activity-Monitoring Device Syncing" (now U.S. Pat. No. 8,745,247), which is a continuation of U.S. patent application Ser. No. 13/769,241 filed Feb. 15, 2013 and entitled "Wireless Portable Biometric Device Syncing" (now U.S. Pat. No. 8,738,925), which claims the benefit of U.S. Provisional Application No. 61/749,911 filed Jan. 7, 2013 and entitled "Systems and Methods for Wireless Portable Biometric Device Syncing." The foregoing applications are hereby incorporated by reference in their entirety for all purposes.

CROSS-REFERENCE TO RELATED APPLICATIONS

U.S. patent application Ser. No. 13/156,304 filed Jun. 8, 2011 and entitled "Portable Monitoring Devices and Methods of Operating Same" is related and is hereby incorporated by reference.

BACKGROUND

The use of wired and wireless portable electronic devices continues to grow. Many individuals own and use multiple portable devices, each of which has one or more particular functions, including cell phones, personal digital assistants, navigation devices, and body monitoring or fitness-oriented devices. These devices are often used in addition to non-portable devices such as desktop computers. It is expected that these various devices can communicate with the internet and/or with each other for uploading and downloading data or otherwise transferring data. One example of a portable biometric monitoring device that communicates with the internet and other devices is a monitoring device that is intended to be small and easily worn on or about the body. When monitored data is collected by the device, it is desirable to regularly and frequently transfer the data (sometimes after on-board processing and sometimes before on-board processing) to other computing devices so that the user can easily review the data or possibly operate on it.

Applications or websites accessed from computing devices may allow users to see and interact with their data, providing further motivation to reach their lifestyle goals.

BRIEF DESCRIPTION OF FIGURES

The various embodiments disclosed herein are illustrated by way of example, and not by way of limitation, in the figures of the accompanying drawings and in which like reference numerals refer to similar elements and in which.

DETAILED DESCRIPTION

Many users of biometric monitoring devices enjoy the ability to view and interact with their data on portable computing devices, but do not like the hassle of managing the storage and transfer of data to these portable devices. For this reason, a seamless syncing experience that requires little or no user interaction is highly desirable. Techniques disclosed herein describe how the device may automatically determine when it should transfer data, freeing the user from the having to remember when they should transfer data. It is also desirable to have a long battery life, secure data transfer, wireless data transfer and high data transfer speeds. The present invention addresses improvements over the prior art on these and other fronts.

More generally, various methods and systems of wirelessly syncing data to and from biometric monitoring devices are disclosed herein including, for example and without limitation, (1) a communication and/or computing device having a wireless transceiver, (2) a biometric and/or environmental sensor device (for example, an activity monitoring device such as any device described and illustrated in U.S. patent application Ser. No. 13/156,304, entitled "Portable Monitoring Devices and Methods of Operating Same", filed Jun. 8, 2011) having one or more sensors and active and/or passive wireless transceiver circuitry. The sensor device gathers and stores data during its operation and can sync its stored data to the communication device.

Figure 1:
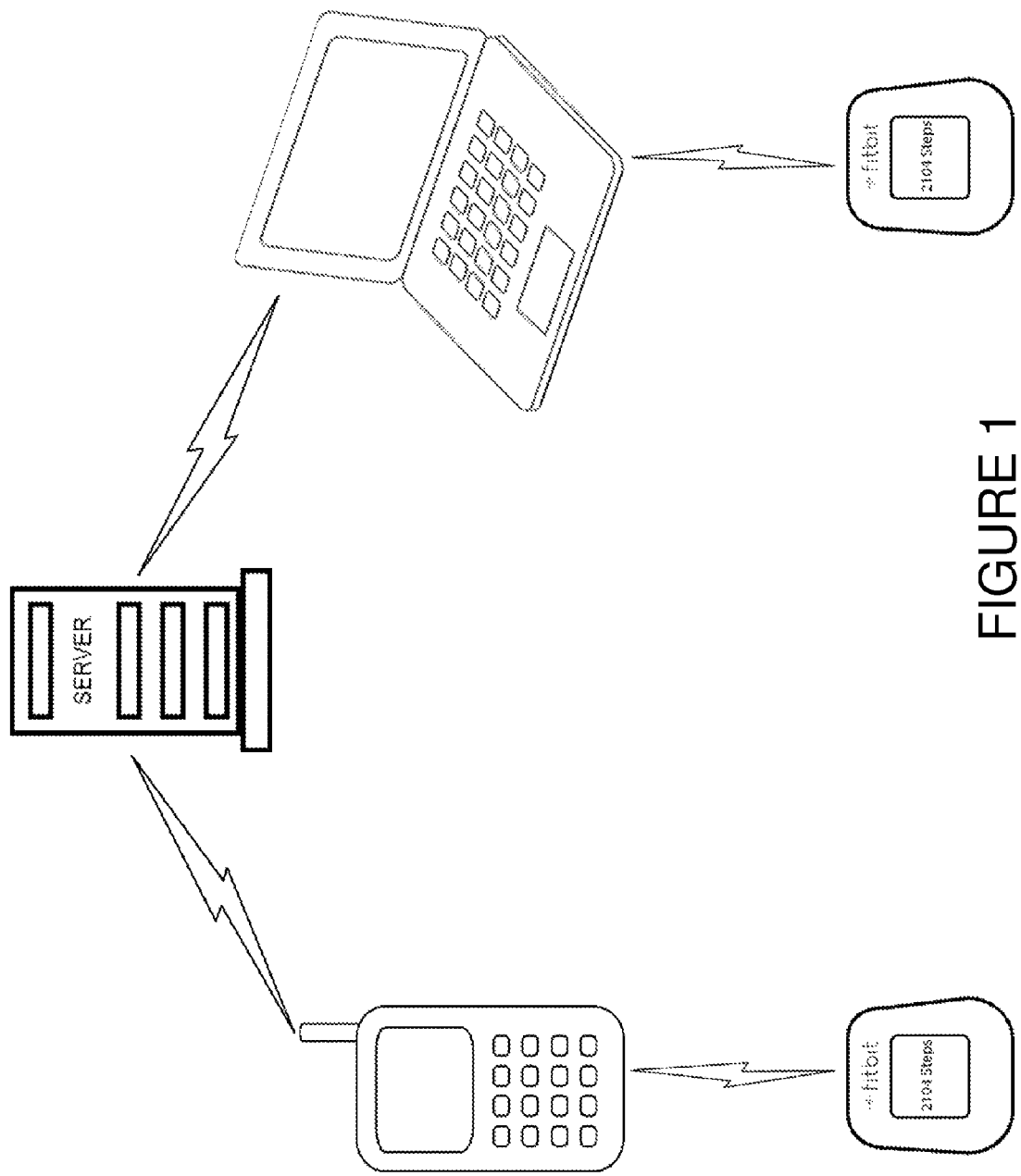
FIG. 1 shows how a sensor device may sync data to a server using a portable communication device such as a smartphone or laptop as a network tunnel.
Figure 2:
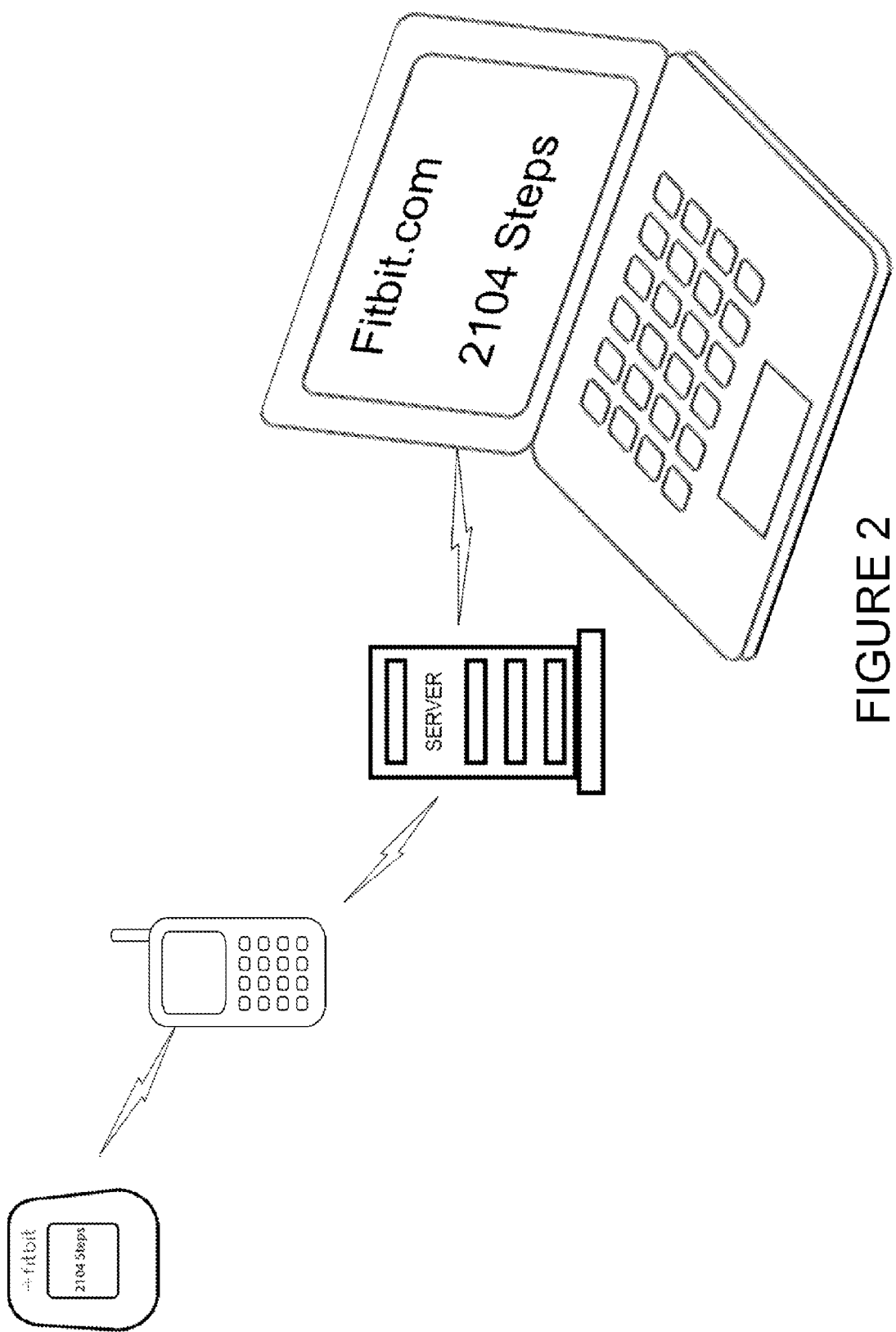
FIG. 2 shows how a sensor device may sync data to a server that subsequently distributes the data to other devices such as a laptop to enable the user to view and interact with their data.

In this document, the term "sync" refers to the action of sending and/or receiving data to and/or from a computing device and/or portable communication device as seen in FIG. 1. "Sync" may also be used in reference to sending and/or receiving data to and/or from another computing device or electronic storage devices including but not limited to a personal computer, cloud based server, and database. In some embodiments, a sync from one electronic device to another may occur through the use of one or more intermediary electronic devices acting as a portal. For example, data from a personal biometric device may be transmitted to a smart phone that relays the data to a server. The data may then be viewed on other server-connected devices as shown in FIG. 2.

In the case where the data is relayed from a portable biometric device to a computing device through a communication device, the data may indicate to the communication device that the data should be relayed. For example, the data transmission may contain a code that tells the communication device to relay the data. In another example, the relay indicator may not be an addenda to the message, but rather something inherent to the data itself. For example, if the data has a certain type of encryption, the encryption type may indicate that the communication device should forward the data to a computing device. Note that being unencrypted may be considered an encryption type.

Syncing may occur through wired and/or wireless connections including but not limited to USB, Wi-Fi, WiMAX, Mobile telephony (i.e. cellular networks), Bluetooth, Bluetooth Smart, NFC, RFID, and ANT.

In this document, the term "communication device" refers to an electronic computing device having a wireless transceiver. Communication devices may include but are not limited to cell phones, smart phones, tablet computers, netbooks, laptops, personal data assistants, and desktop computers.

In this document, the term "client" refers to client software or a client device that primarily acts as an access portal to a server. The term "server" refers to a server in communication, directly or indirectly, with one or more of the device and the client. In some embodiments, the server may be eliminated from this system, making the client serve the functions of both the client and server.

Devices which are not considered portable biometric devices, but may use syncing methods according to the invention disclosed herein include but are not limited to portable or non-portable devices such as weight scales, body fat scales, exercise equipment, blood glucose meters, pulse oximeters, blood pressure cuffs, and, in one embodiment mobile phones. A weight scale may be used to describe a device which has a platform capable of supporting the weight of a user. The scale may contain a plurality of sensors including, but not limited to Body Impedance or BIA sensors to measure body fat, weight sensors, ambient light sensors, and photoplethysmographic sensors.

The portable biometric monitoring device (also referred to herein simply as "the device") has a shape and size that is adapted to be easily worn about the body of a user. The device collects one or more types of physiological and/or environmental data from embedded sensors and/or external devices and communicates or relays such information to other devices or other internet-viewable sources. Notably, the device collects data regarding altitudinal transitions (e.g. climbing stairs) and ambulatory motion (e.g. walking or running). In one example, the user is wearing a device which monitors certain conditions through one or more sensors, and collects data from the sensors. For example, the device can calculate the user's step count from collected data, store the step count, then subsequently transmit user data representative of the step count to an account on a web service (such as www.fitbit.com, for example) where the user data is stored, processed, and viewed by the user. Indeed, the device may monitor, measure or calculate many other physiological metrics in addition to, or in place of, the step count. These include, but are not limited to, energy expenditure, floors climbed or descended, heart rate, heart rate variability, heart rate recovery, location and/or heading (e.g., using global positioning system (GPS) components), elevation, ambulatory speed and/or distance traveled, swimming lap count, bicycle distance and/or speed, blood pressure, blood glucose, skin conduction, skin and/or body temperature, electromyography, electroencephalography, weight, body fat, and respiration rate. The circuitry used to sense and/or calculate these metrics is referred to herein as biometric circuitry. The device may also measure or calculate metrics related to the environment around the user such as barometric pressure, weather conditions, light exposure, noise exposure, and magnetic field.

The device may incorporate one or more user interface and/or feedback methods such as visual methods, auditory methods, or haptic methods (such as touch input or vibration). The device may display the state of one or more of the information types available and/or being tracked. For example, information can be displayed graphically, or conveyed by the intensity and/or color of one or more light emitting diodes (LEDs). The user interface may also be used to display data from other devices or internet sources. The device may also provide haptic feedback to the user through, for instance, the vibration of a motor or a change in texture or shape of the device.

In one embodiment, the device may not have a display. The device may instead communicate information to the user using one of the other user feedback methods described herein (e.g. one or more LED's, haptic feedback, audio feedback). In another embodiment, the device may not communicate information to the user directly. Instead, the user may view their information on one or more secondary computing devices in direct or indirect communication with the device. In the case that the communication is indirect, data may be transferred from the device to one or more intermediate communication devices (e.g. smart phone) which then forwards the information to the secondary computing device used to view data. For example, data may be transferred from the device through a smartphone to a server that hosts a website containing the user's data. The user can then view their data through a compatible web browser on any internet connected computing device.

Figure 12:
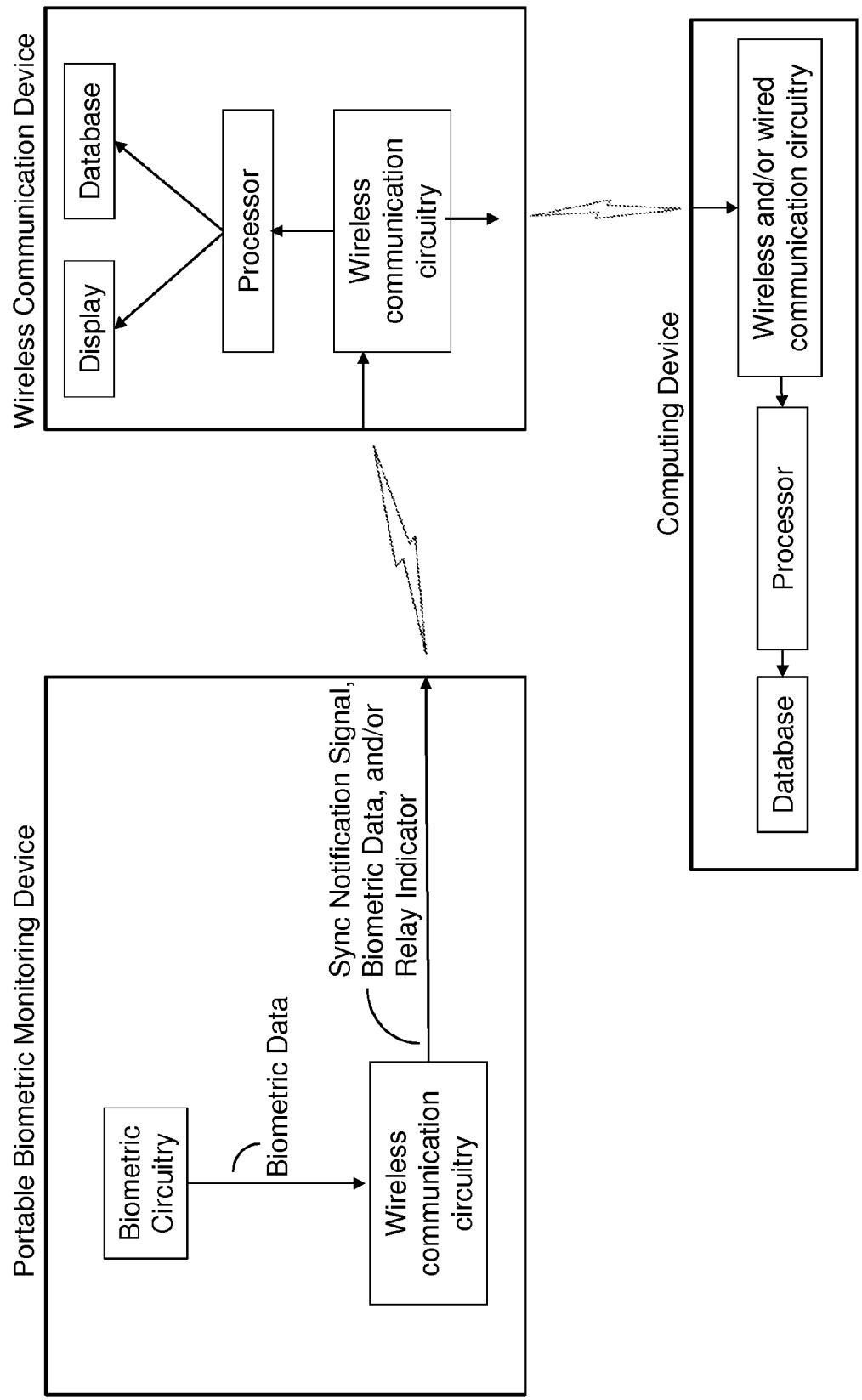
FIG. 12 shows an embodiment where a portable biometric device wirelessly sends data to a wireless communication device that relays the data to a computing device.

An embodiment where a portable biometric device wirelessly sends a sync notification signal to prompt a second nearby wireless communication devices to communicate with the device is shown in FIG. 12. Once a communication link has been established, biometric data may be sent with or without an indication that the data should be relayed to a third computing device. If the wireless transmission does not indicate that the data should be relayed, the data is displayed and/or stored on the second wireless communication device. If the wireless transmission indicates that data should be relayed, the wireless communication device communicates over one or more wired or wireless communication networks to relay the data to a third computing device which stores the data in a database. The relayed data may also be stored or displayed on the wireless communication device.

Figure 13:
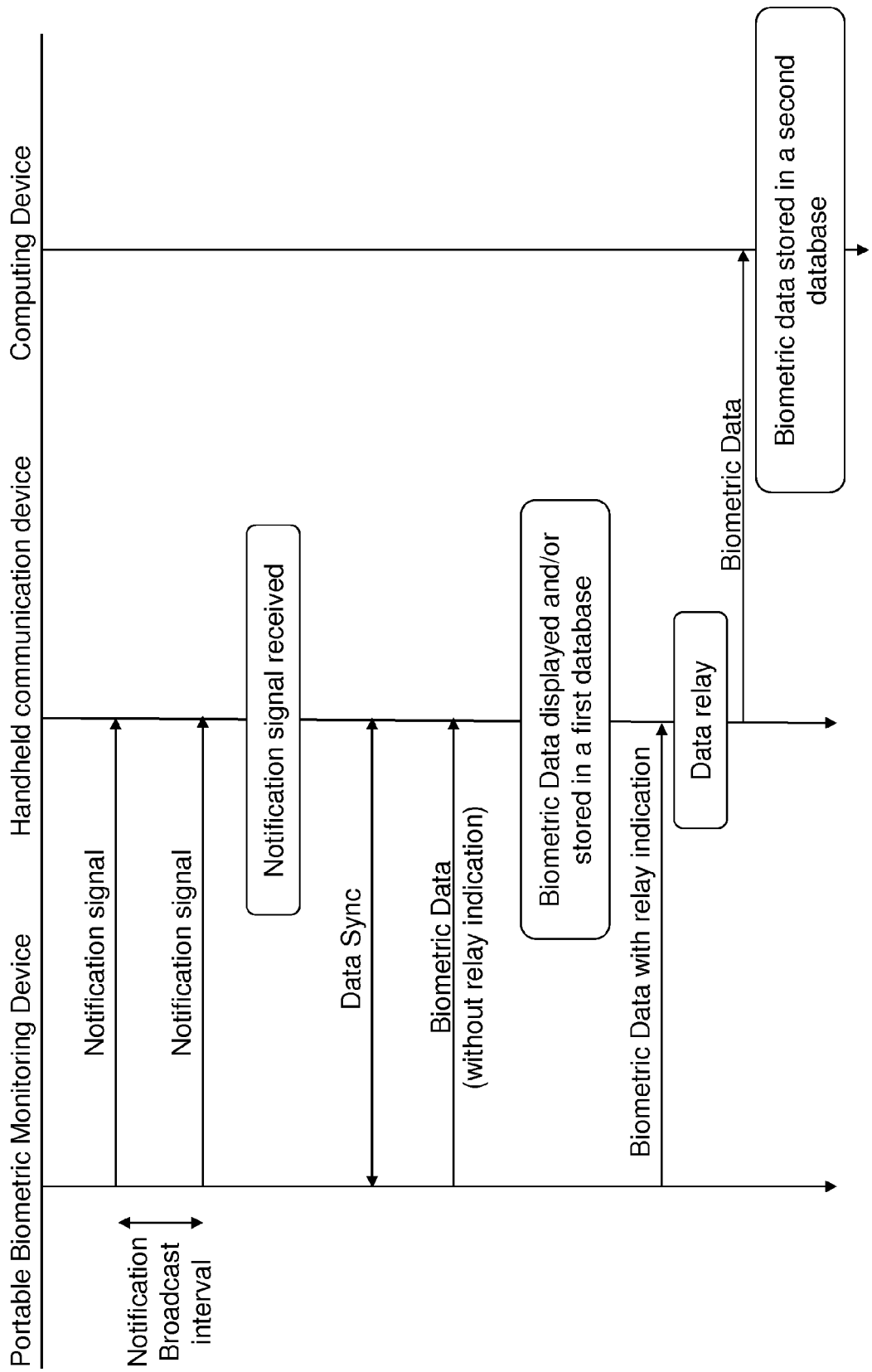
FIG. 13 shows one example of communications between a portable biometric device, handheld communication device and computing device.

One example of communications between a portable biometric device, handheld communication device and computing device is illustrated in FIG. 13. Initially the portable biometric device may send a notification signal to notify any nearby handheld communication devices of its presence. Once a handheld communication device receives one of these alerts, the handheld communication device may sync data with the portable biometric device. Biometric data which is sent to the communication device without an indication that the data should be relayed is displayed and/or stored on a first database on the communication device. Data with a relay indication is forwarded onto a computing device where the data is stored in a second database. Relayed data may also be displayed and stored on the communication device.

Figure 14:
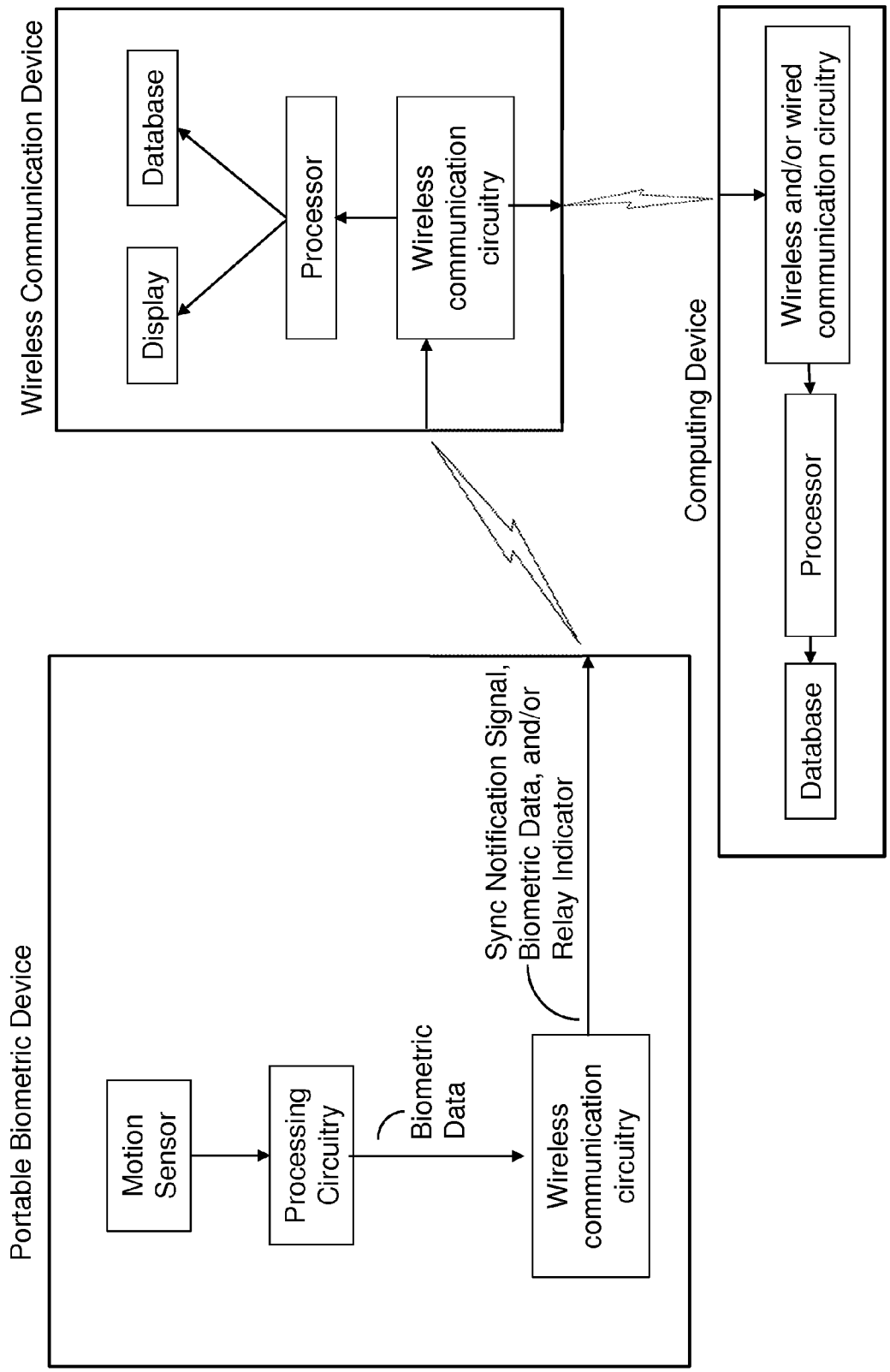
FIG. 14 shows an embodiment where a portable biometric monitoring device contains a motion sensor wirelessly sends data to a wireless communication device that relays the data to a computing device.

In one embodiment a portable biometric monitoring device contains a motion sensor. Motion sensor data is operated on by processing circuitry to create biometric data. The portable biometric device wirelessly sends a sync notification signal to prompt a second nearby wireless communication devices to communicate with the device. Once a communication link has been established, biometric data may be sent with or without an indication that the data should be relayed to a third computing device. If the wireless transmission does not indicate that the data should be relayed, the data is displayed and/or stored on the second wireless communication device. If the wireless transmission indicates that the data should be relayed, the wireless communication device communicates over one or more wired or wireless communication networks to relay the data to a third computing device which stores the data in a database as shown in FIG. 14. The relayed data may also be stored and/or displayed on the wireless communication device.

Figure 15:
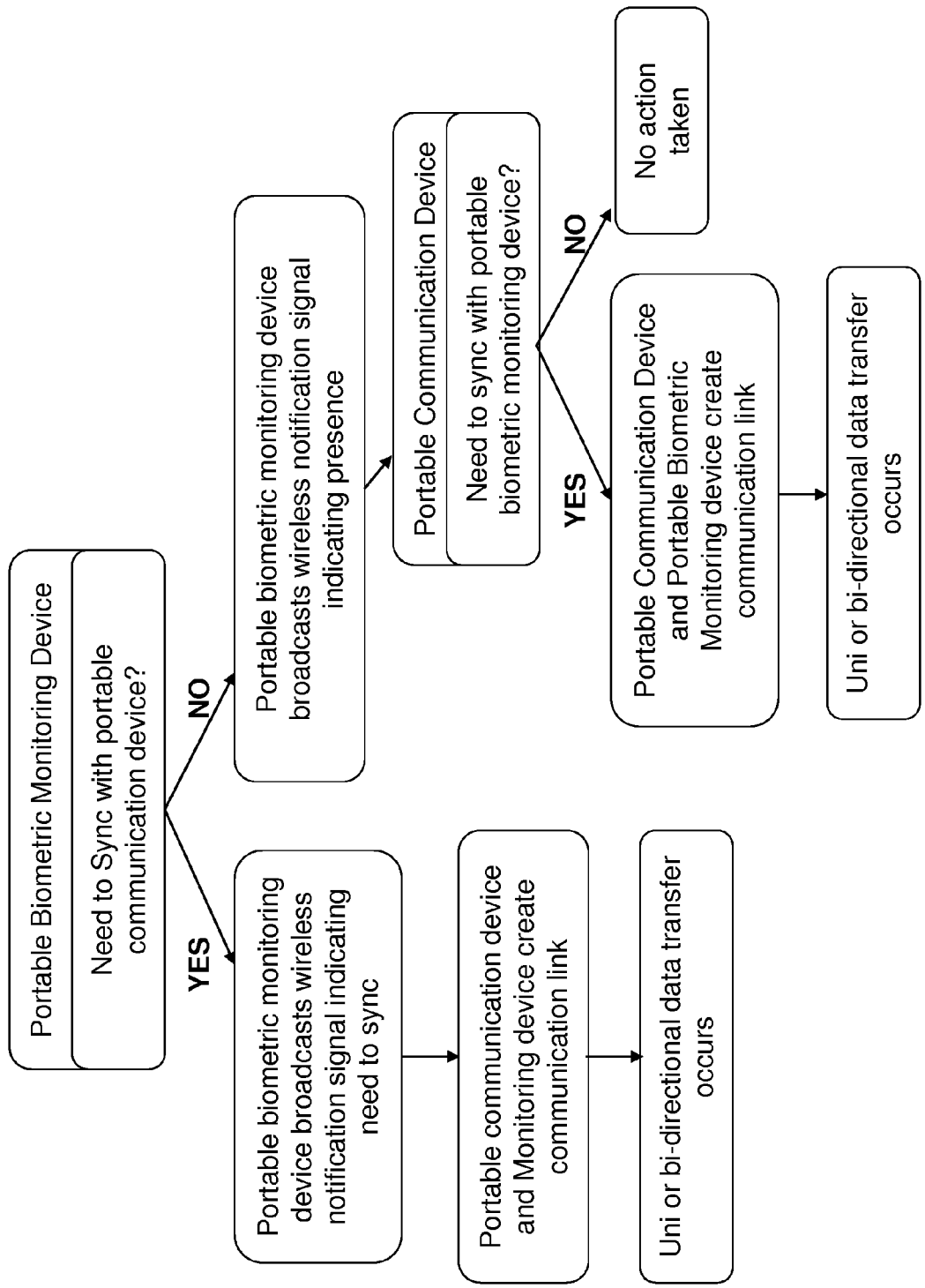
FIG. 15 shows the steps which occur when the portable biometric monitoring device broadcasts a notification signal to proximal communication devices.

An exemplary set of operations executed when the portable biometric monitoring device intermittently (i.e., periodically or aperiodically) broadcasts a notification signal to proximal communication devices is shown in FIG. 15. The portable biometric monitoring device may indicate, in the notification signal or a characteristic of the notification signal, whether the portable biometric monitoring device seeks (or requests) to sync or establish a communication link with the communication device. In the case that the portable biometric monitoring device does not seek to establish a communication link with the communication device, the communication device may still take action to establish a communication link and sync or not (e.g., the communication device may itself have data to be transmitted to the portable biometric monitoring device in a sync operation and thus may seek to establish a communication link even if the portable biometric monitoring device does not). In the case that the portable biometric monitoring device does seek to establish a communication link with the communication device, the communication device can decide to accept or reject the portable biometric monitoring device's request to establish a communication link and/or sync.

Data from the portable biometric device such as those disclosed herein may be used by an application or service located on a portable communication device (e.g. smart phone), computing device (e.g. personal computer), portable computing device (e.g. laptop or tablet computer), and/or accessed through a network such as the internet through a network connected browser or application. Users of portable biometric monitoring devices may have accounts on such applications or services which allow them to retrieve data relevant to themselves or other users. An account may enable a user to visualize their data, modify data visualizations, modify or enter additional or existing data, manage their devices, and/or interact with other users. Data synced from the portable biometric monitoring device may be used for account features including but not limited to a leader board where the user is ranked compared to other users such as friends, rankings of members of a group of users, and badge awards to reaching various goals. The user account may also automatically provide recommendations to the user so as to help them reach one or more goals including but not limited to increasing or decreasing their weight, body fat, time asleep, quality of sleep, calorie burn, activity level, resting heart rate, active heart rate, normal heart rate, steps taken, distance walked and/or run, and floors climbed. These recommendations may aid the user in short term and/or long term goals. For example, if a user has been less active over the last month and has started to gain weight, they may be recommended to be more active this month through a notification on their web based account. On a shorter time scale, a user may be recommended to eat less for dinner if they were not very active and had a large lunch earlier in the day. In order for such short term recommendations to be relevant to the user's current state, data synced from their device which help determine the recommendation is preferably transferred frequently and/or whenever there is new data on the device relevant to such a recommendation.

In one embodiment, this communication device may have foreground and background operating system states. In foreground mode, the function or functions that perform the detection of the sensor device and syncing of data is running in the foreground of the operating system of the communication device. In the background mode, this function or functions are running in the background of the operating system of the communication device. Typically functions which are run in the background have no or minimal visual indications that they are running on the display of the communication device. Often functions which run in the background run when the display of the device is off and/or when the communication device is in a "sleep" or "locked" mode.

Data may be synced to the communication device for the data to be displayed to the user on the communication device. The data may also be stored to a database in the memory of the communication device.

Sensor Device Broadcasts

In order to enable initiation of a data sync operation, a sensor device may continuously or intermittently (i.e., periodically or aperiodically) transmit wireless packets or other information-bearing transmissions referred to herein as notification signals. The frequency of periodic packet transmissions may vary to balance power consumption and the time to detection. These packets may contain information such as the unique identifier of the sensor device, an identifier that indicates the type of sensor device, a unique identifier of the user of the device, and/or data which indicates some internal state of the device. This internal state information may include but is not limited to an indication of (i) whether the device has new data that the device needs to sync, (2) whether the device wants to sync, (iii) the last time that the device has synced, (iv) the battery level of the device, and/or (v) a flag which indicates whether the device has synced within a specified or predetermined time period (e.g., within the last 15 minutes, last hour, etc.). The information in the packets may be separate pieces of data or combined into a single piece of data. For instance, a device identifier represented by a long or short integer may be separate from a sync indicator (itself represented by a bit, or long or short integer) that indicates whether the device has new data that needs to be synced, or the device identifier and sync indicator may be combined within a single short or long integer.

Figure 17:
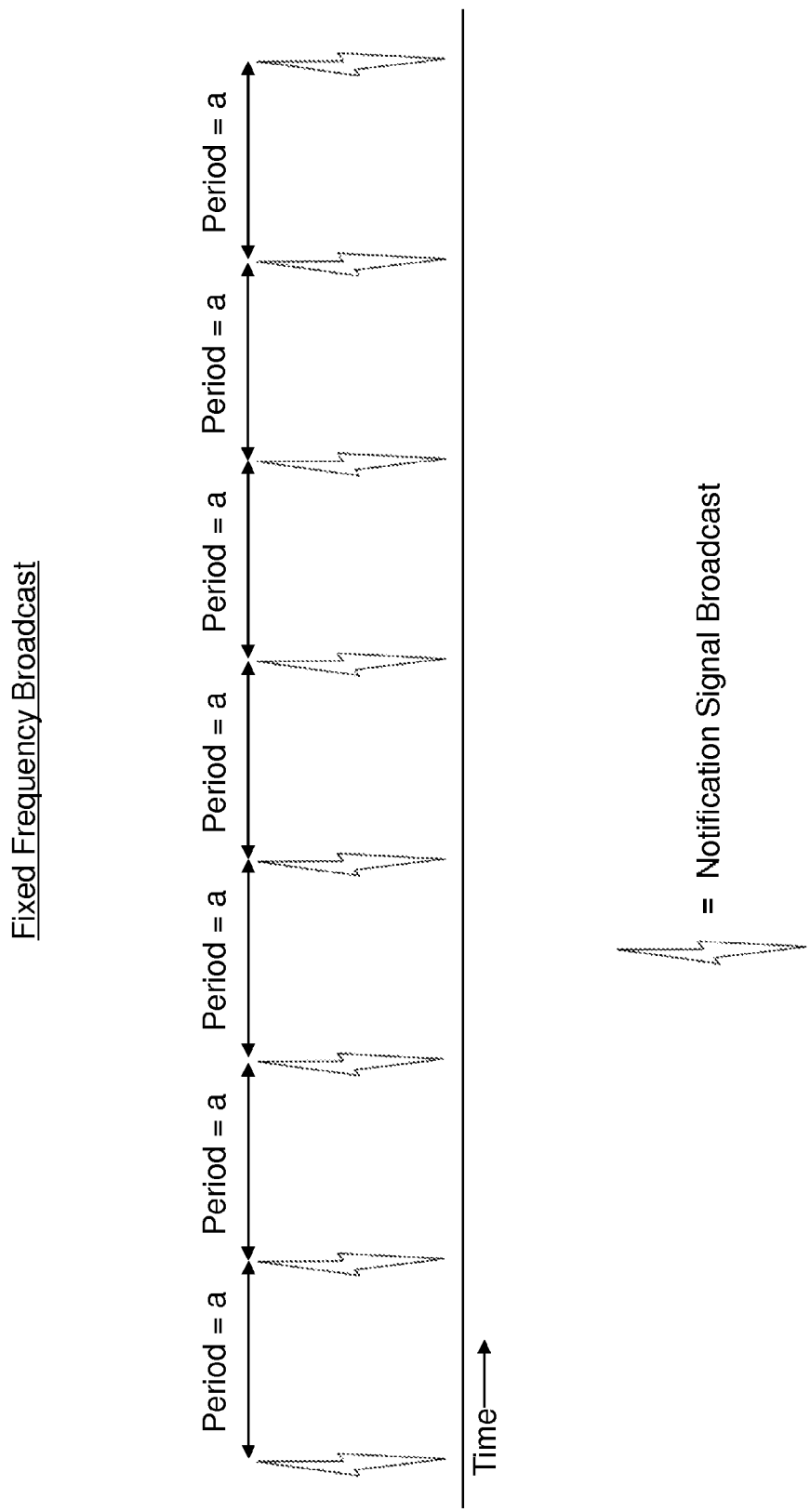
FIG. 17 shows fixed frequency notification signal broadcast timing.

In one embodiment, the sensor device may broadcast a signal with a fixed frequency to any communication devices in the proximity as shown in FIG. 17. In a number of embodiments, for example, the period "a" may be equal to or less than ten seconds. In other embodiments, the period "a" may be greater than ten seconds. This may enable low latency communication link creation while avoiding unnecessary communication between the communication device and the sensor device. Unnecessary communication is undesirable as it consumes power. The communication device may constantly listen for these signals. The signal may indicate to the communication device whether or not the sensor device needs to communicate.

Figure 18:
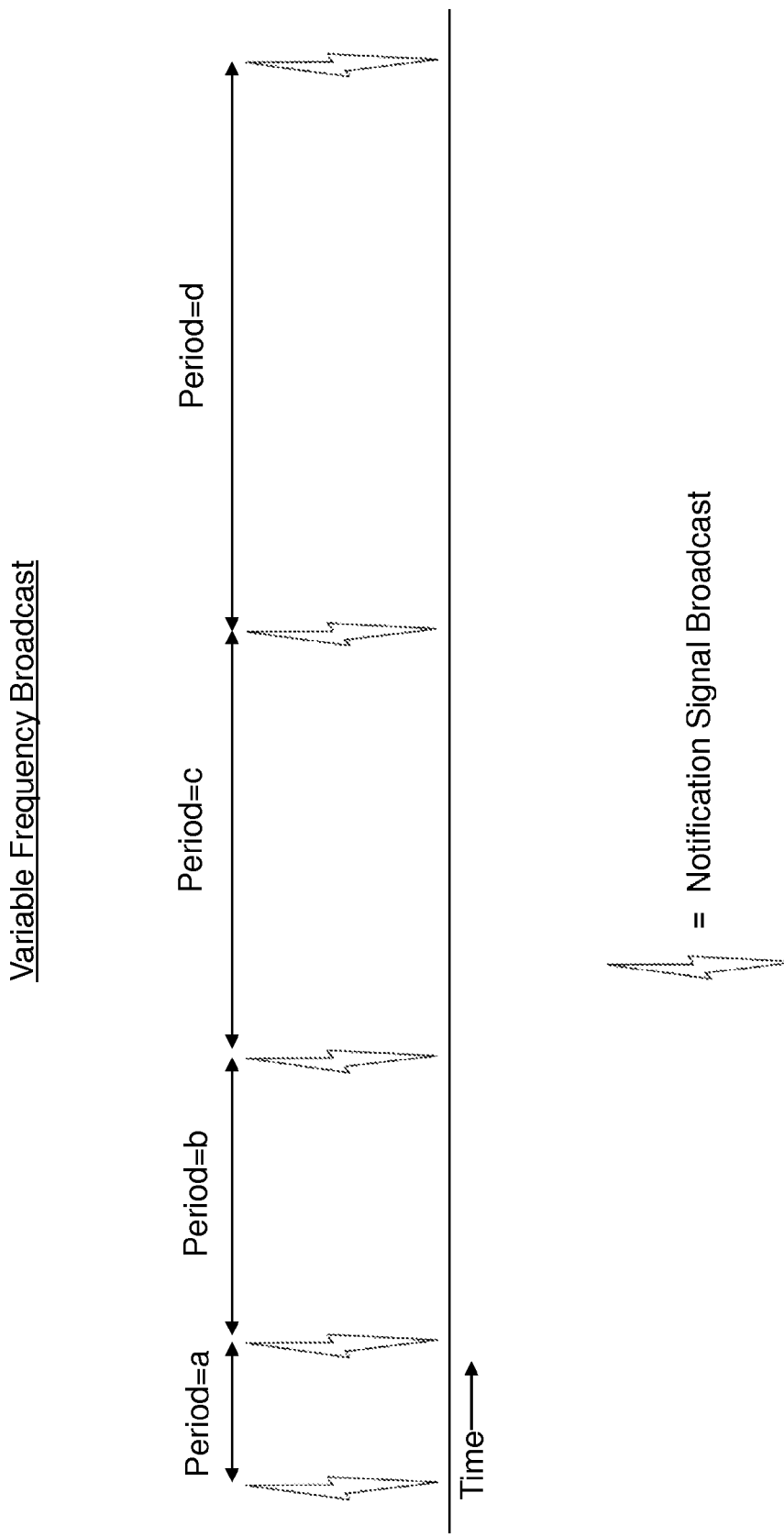
FIG. 18 shows variable frequency notification signal broadcast timing.

In one embodiment, illustrated in FIG. 18, variable frequency notification signal broadcast timing is used. The period "a," "b," "c," and "d," may all be different periods of time. In some embodiments, these values may be related algorithmically. In one embodiment, the portable biometric monitoring device may send out a notification signal broadcast at a minimum of every 2 seconds. If the portable biometric monitoring device doesn't get a response from a communication device, it may increase that interval by 1 minute. There may be a maximum interval of 30 minutes for example. If the device does get a response, the interval may revert to the minimum interval of 2 seconds. This strategy could reduce battery drain when there is no communication device to sync to. Algorithms for changing the frequency other than that already described may also be used. In other embodiments, the frequency may change based on syncing criteria, update thresholds or user interactions.

Figure 19:
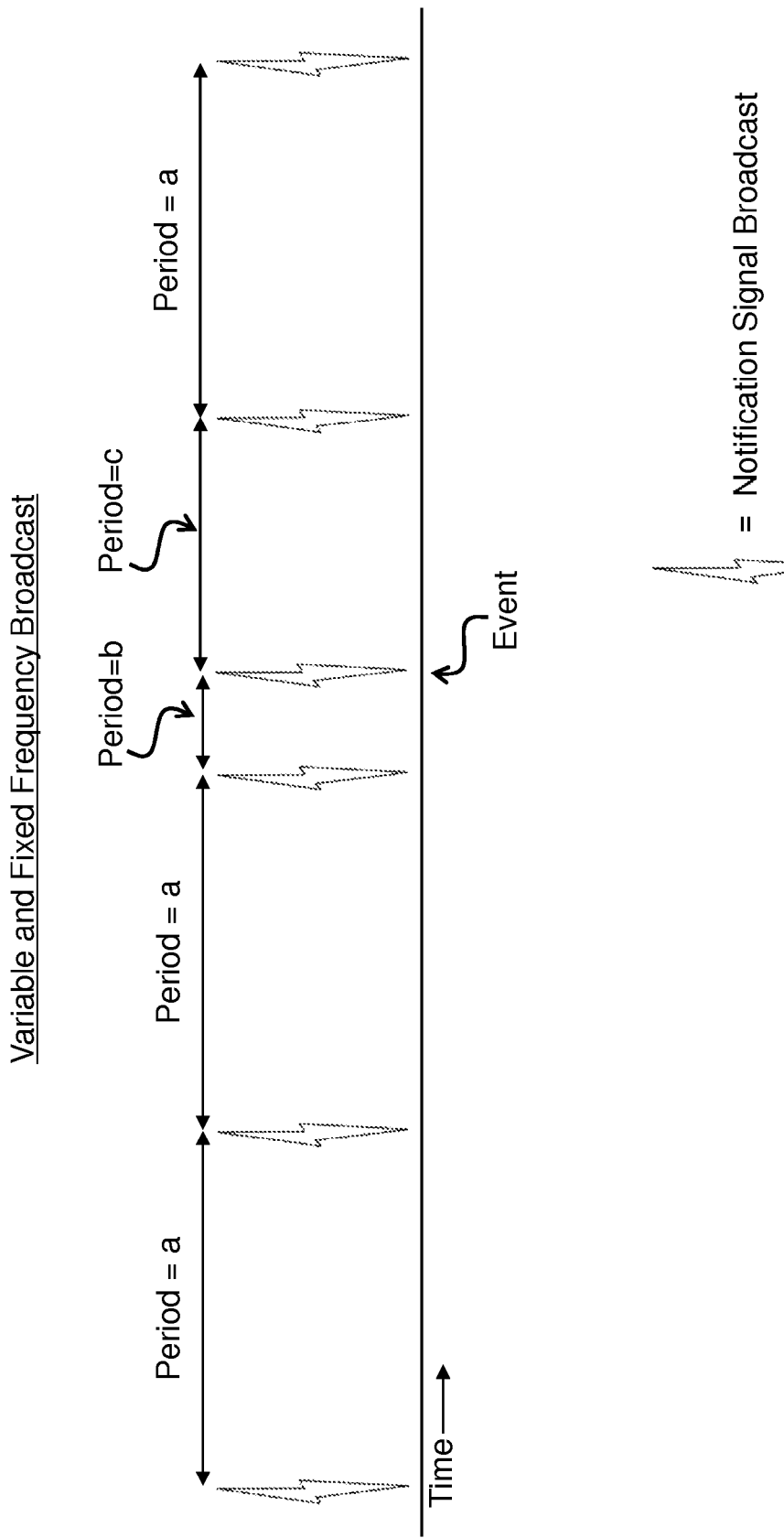
FIG. 19 shows a mix of variable and fixed frequency notification signal broadcast timing.

In one embodiment, a mix of variable and fixed frequency notification signal broadcast timings are used. The portable biometric monitoring device may broadcast a signal with a period "a" as seen in FIG. 19. In some cases, a broadcast may occur a time period "b" after the last broadcast. The period "b" may be greater or less than "a." In some embodiments, an event such as reaching a biometric data update threshold may trigger a change in period. After this event, the next broadcast may occur a period "c" later where "c" is less than, equal to or greater than "a."

Figure 20:
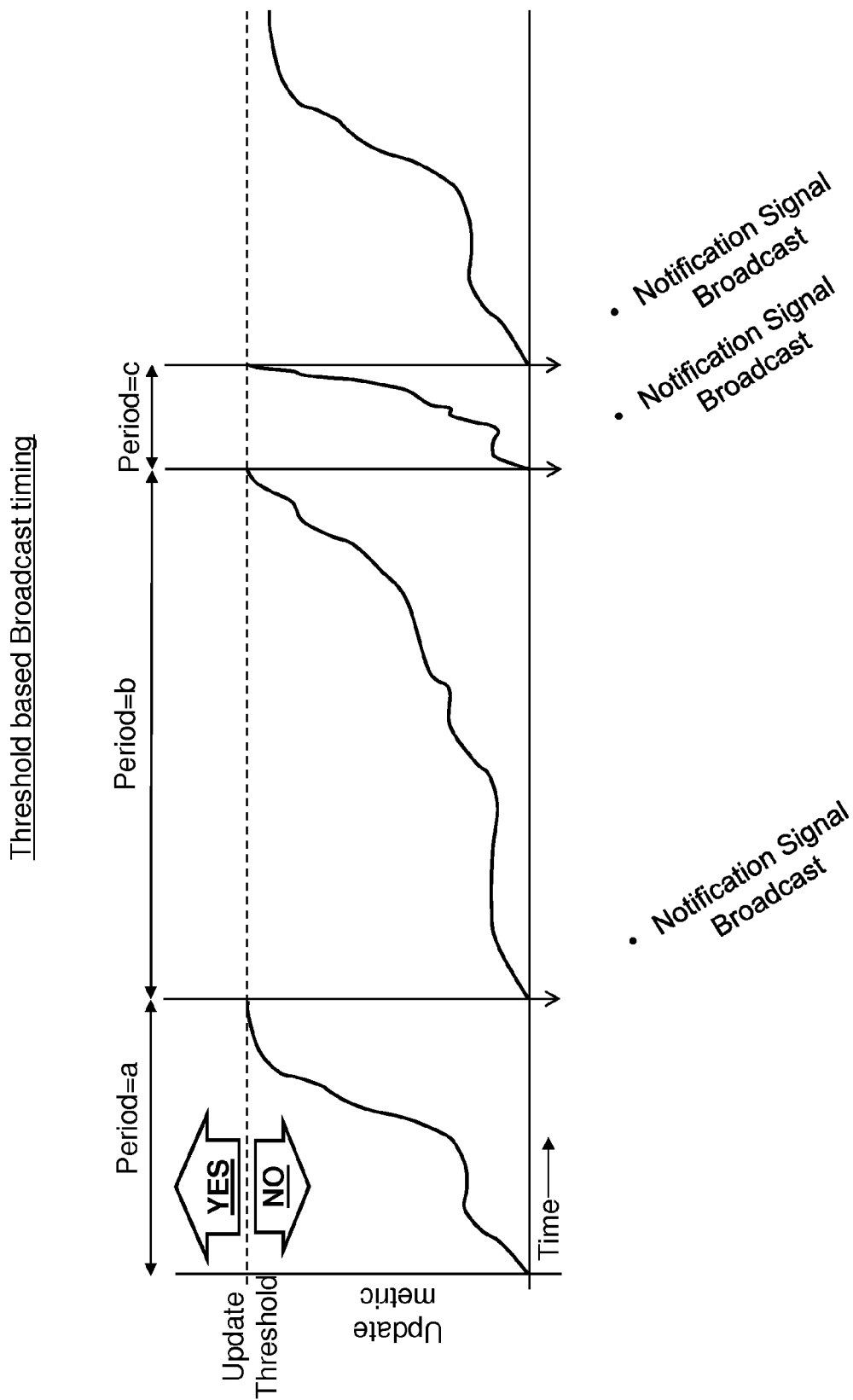
FIG. 20 shows a broadcast timing scheme where an update threshold is used to determine the time at which a broadcast occurs.

The portable biometric monitoring device may need to sync if it has accumulated a certain amount of biometric data. For example, the portable biometric monitoring device may determine that it needs to sync if it has acquired new biometric data and it has been longer than 15 minutes since the last sync. Other criteria or update thresholds (e.g., corresponding to a threshold change in the biometric data acquired) that may be used to determine when a communication link should be established are disclosed herein. FIG. 20 shows a broadcast timing scheme where an update threshold is used to determine the time at which a broadcast occurs. The period "a," "b," and "c" may be wholly or in part determined by the amount of time it takes for an update metric to reach a fixed or time varying threshold.

Figure 21:
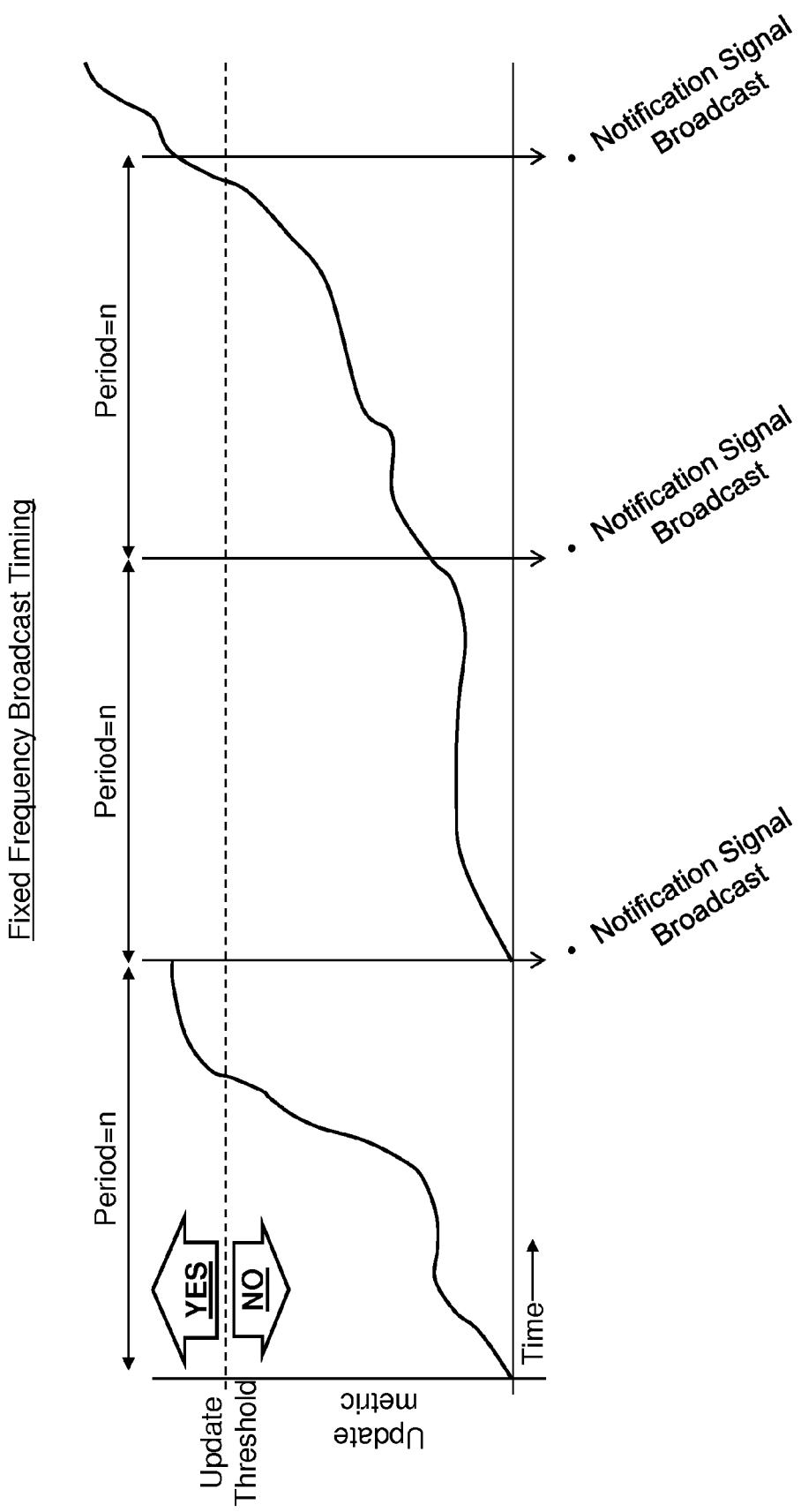
FIG. 21 shows how a fixed frequency broadcast timing scheme may define a period "n" between notification signal broadcasts.

FIG. 21 illustrates how a fixed frequency broadcast timing scheme may define a period "n" between notification signal broadcasts. This period "n" may be independent of the value of an update metric and whether the value is above, below or equal to an update threshold.

Figure 22:
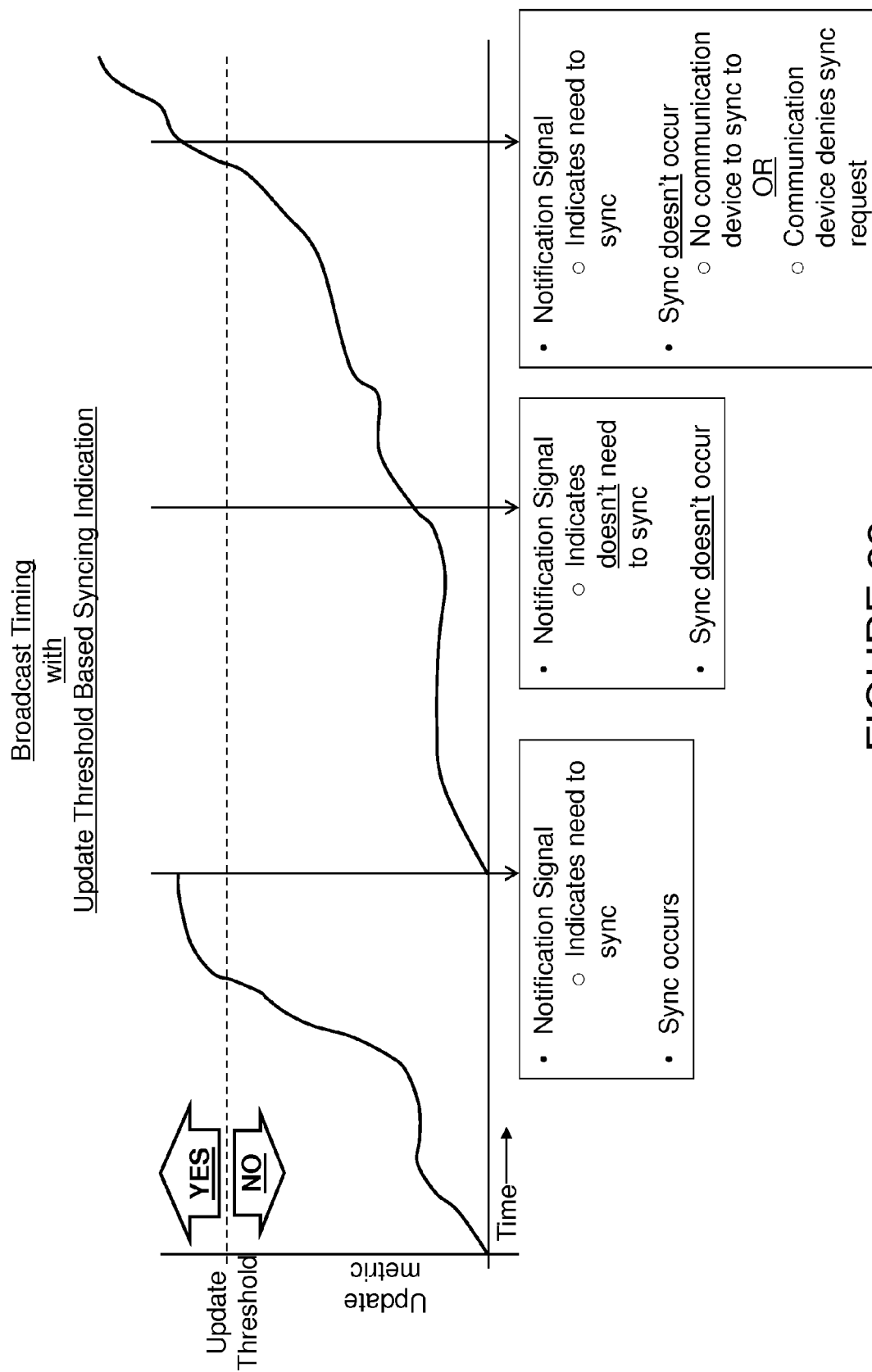
FIG. 22 shows how the indication of whether or not the portable biometric device seeks the establishment of a communication link with a communication device is determined using an update threshold.

The indication of whether or not the portable biometric device seeks the establishment of a communication link with a communication device may be determined by comparing an update metric to an update threshold as seen in FIG. 22. When the time for a broadcast occurs (either with a fixed or variable frequency), the portable biometric device checks to see if an update metric has met an update threshold. If the threshold has been met, then the notification signal will be broadcasted with an indication that the portable biometric monitoring device seeks to establish a communication link and/or sync. If the update threshold has not been met, the notification signal will indicate that the portable biometric monitoring device does not need to establish a communication link and/or sync. Note that in one embodiment the indication does not necessarily determine whether or not a communication link is established and/or sync will occur. The communication device can use the indication as an aid in determining whether or not to establish a communication link and/or sync.

The signal may also notify the communication device that it is available for communication, but does not need to communicate. This allows the communication device to open a communication link with latency equal to the periodicity broadcasted signal. The communication device may need to open a communication link for reasons including but not limited to a user directed pairing, user directed data sync, update of the device firmware, biometric configuration data update (e.g. stride length, height), device configuration data update (e.g. alarm clock settings, display settings).

In one embodiment, the communication device and the sensor device may communicate using the Bluetooth Smart protocol. The sensor device may intermittently broadcast one of two UUID's (universally unique identifiers) to the communication device which is constantly listening for broadcasts. The first UUID corresponds to a Bluetooth service which is used to sync new data from the sensor device. This service is configured to start any programs on the communication device necessary to sync the new data from the sensor device. The second UUID corresponds to a Bluetooth service which is only used when a program on the communication device needs to send data to the sensor device.

The communication device may monitor its wireless input sources for incoming wireless packets and analyze any received packets in order to detect the sensor device as the source of their transmission and decide whether to sync with the sensor device. The function or functions within the communication device that monitors input sources for and analyzes packets may be embedded within the operating system of the communication device and/or in an application or applications that are launched by the operating system of the communication device (i.e., the input monitoring and/or packet analysis functions may be implemented by execution, within one or more processors of the communications device, of programmed instructions that form part of the communication device operating system and/or application programs). The packet detection functionality may be automatically launched or executed by the operating system or can be initiated or directed by the user or users of the communication device. If the functionality is partially or fully within an application, application or applications may be launched automatically by the operating system or launched by the user or users of the communication device. The packet detection functionality may also be split between the operating system and applications. The functionality can execute or run in any priority or mode (active, foreground, background, etc.) on any processor within the communication device. The functionality can also run simultaneously with other functions on the same communication device. If the functionality has already been launched (i.e., implemented through execution of programmed instructions), the operating system can choose to execute or re-execute the functionality, which might be resident in volatile or non-volatile storage or memory of the communication device.

Listening (monitoring input sources) for incoming packets may be carried out periodically in order to lower power consumption (e.g., by powering down or otherwise disabling signal reception functions during intervals in which input sources are un-monitored), or continuously in order to decrease the time to detection ("detection latency"). Also, the frequency of periodic listening events may be varied to balance power consumption and the time to detection. During a previous interaction, a user or computer, either directly via the user interface of the communication device or via a wired or wireless communication mechanism, may specify which aspects of the contents of a wireless packet or sequence of wireless packets should trigger a data sync by the communication device. Any single piece of information or combination of the information in a wireless packet or sequence of packets may trigger a data sync after receipt and analysis of the packets. When the sync is triggered, the communication device may start and complete the syncing process via functionality that is embedded within the operating system of the communication device or via an application that is launched by the operating system of the communication device. The initiation, start, and/or completion of a sync may be performed with or without user interaction using techniques described herein.

Syncing Criteria

A variety of criteria, when met, may cause the communication device and the sensor device to attempt to sync to each other for example and without limitation:

Device Type Syncing Criteria
    Unique Device Syncing Criteria
    New Data Syncing Criteria
    Goal-Based Data Syncing
    Physiological State Syncing Criteria
    User Interaction Syncing Criteria
    Activity Based Syncing
    Timestamp Syncing Criteria
    Location Syncing Criteria
    Data Connection Type Syncing Criteria Each of the foregoing "syncing criteria" (or criterion) is discussed in further detail below and may be applied in combination with any other(s) of the syncing criteria to form a new (compound) syncing criteria. While the embodiments below may specify that a single entity including communication device, sensor device, or server may initiate a sync and or determine that a sync should occur, it should be noted that any communication device, sensor device, server, or a combination thereof may initiate a sync and or determine that a sync should occur based on each of the "syncing criteria" (or criterion). Note that the term "update threshold" may refer to one or more syncing criteria.

Figure 16:
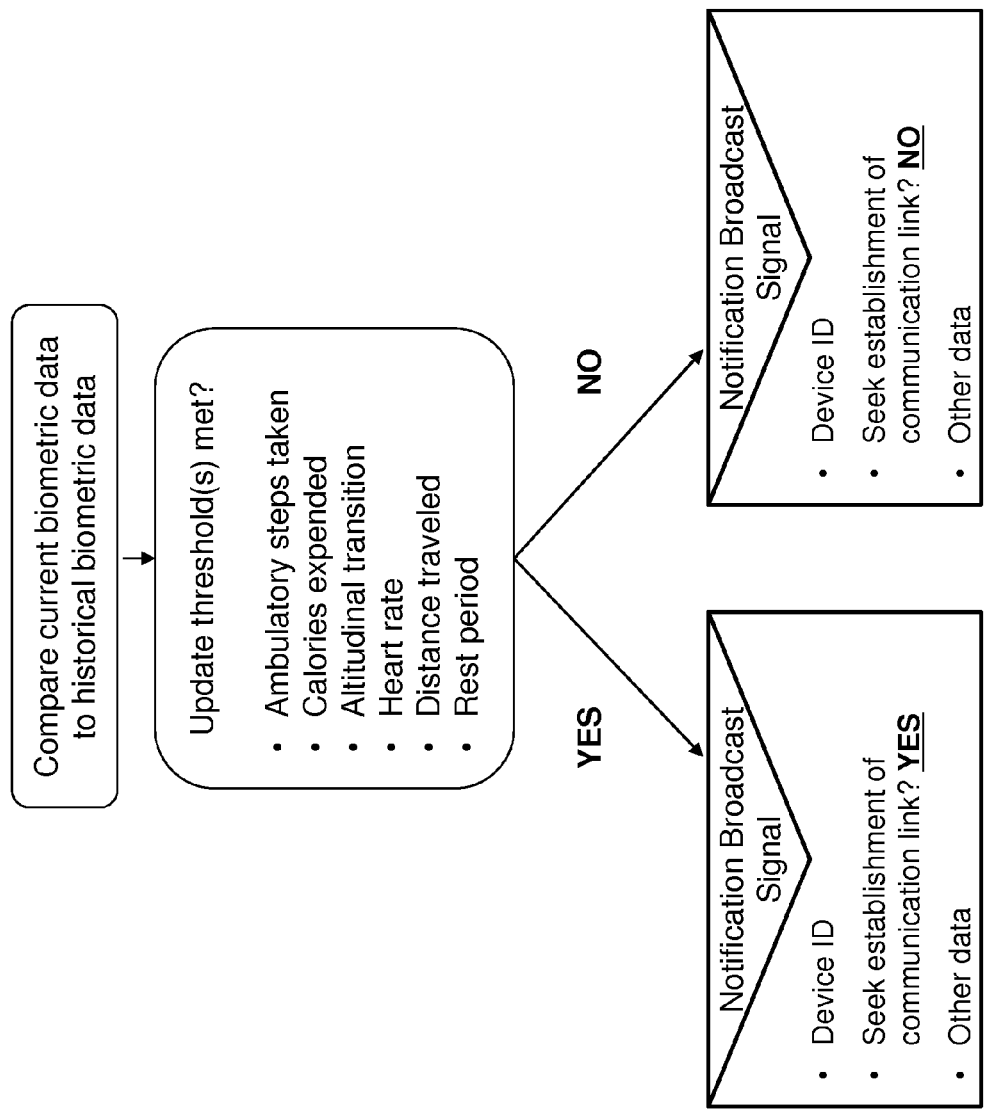
FIG. 16 shows how update thresholds or sync criteria are used to determine whether the portable biometric monitoring device indicates that it would like to seek the establishment of a communication link or not in the portable biometric monitoring device's notification broadcast signal.

FIG. 16 shows how update thresholds or sync criteria are used to determine whether the portable biometric monitoring device indicates that it would like to seek the establishment of a communication link or not in the portable biometric monitoring device's notification broadcast signal. In one embodiment, one or more update thresholds (based on the change in biometric data from the value of the biometric data at the last time that the data was synced to the current value of the biometric data) are used to determine whether or not the portable biometric monitoring device seeks the establishment of a communication link. Note that the list of update thresholds is not exhaustive and is meant only to illustrate several possible update thresholds.

Device Type Syncing Criteria

Figure 3:
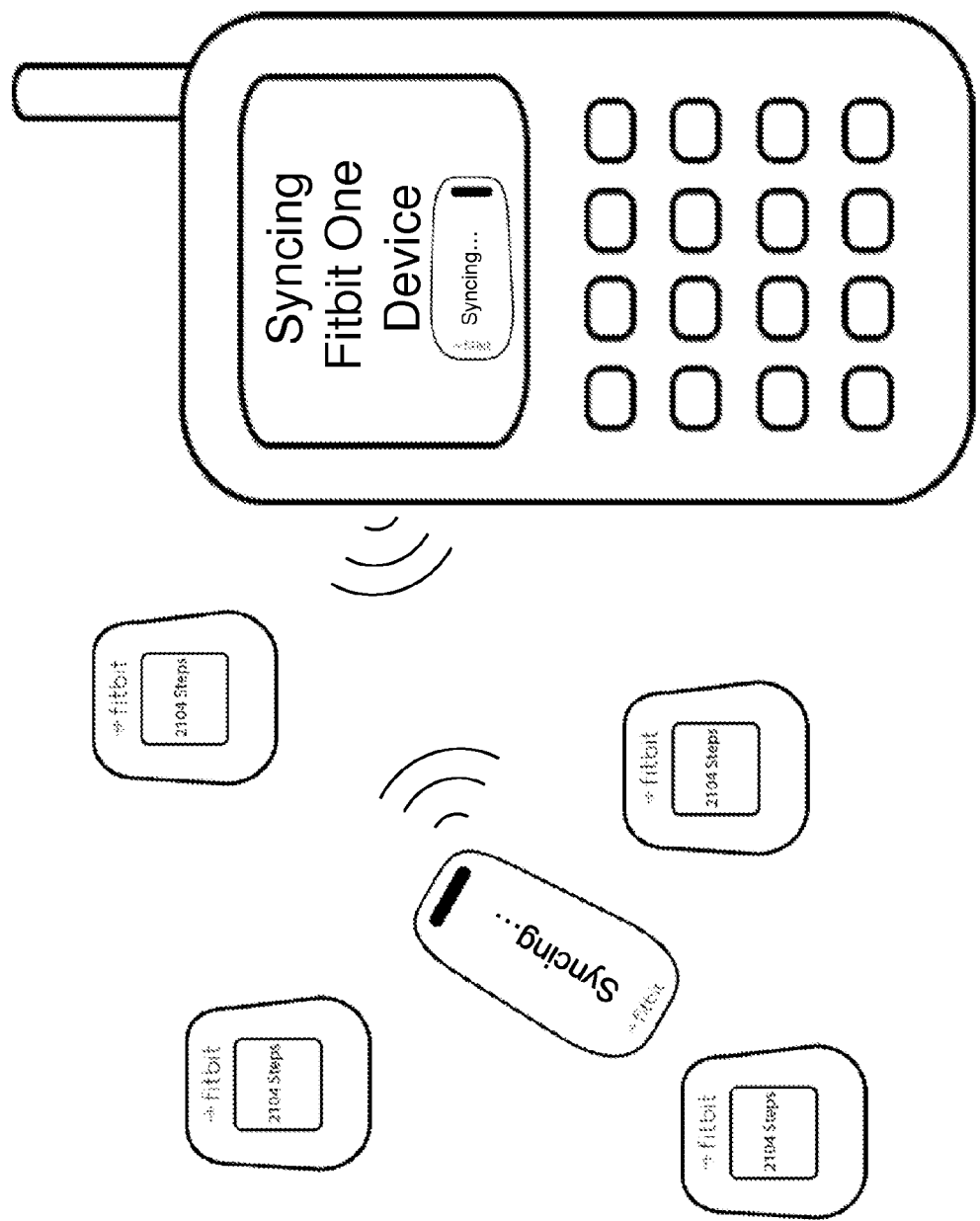
FIG. 3 shows an embodiment where a communication device syncs only a specific type or model of sensor device.

In one embodiment, the communication device might only attempt to sync with a certain type of sensor device. In that case, the communication device will listen for a wireless packet or sequence of wireless packets transmitted by a sensor device and analyze the packets to see they contain an identifier that indicates the type of sensor device. If the identifier is found, a device-type syncing criteria is deemed to be met, and the communication device starts and completes the syncing process in response. Other methods may be used to identify the device type. For example, the type of device may be determined by an NFC tag integrated into the device, an RFID integrated into the device, and/or the wireless protocol that the device communicates with (e.g. device type 'A' uses Bluetooth and device type 'B' uses Wi-Fi). One embodiment of device type syncing criteria is shown in FIG. 3.

Unique Device Syncing Criteria

Figure 4:
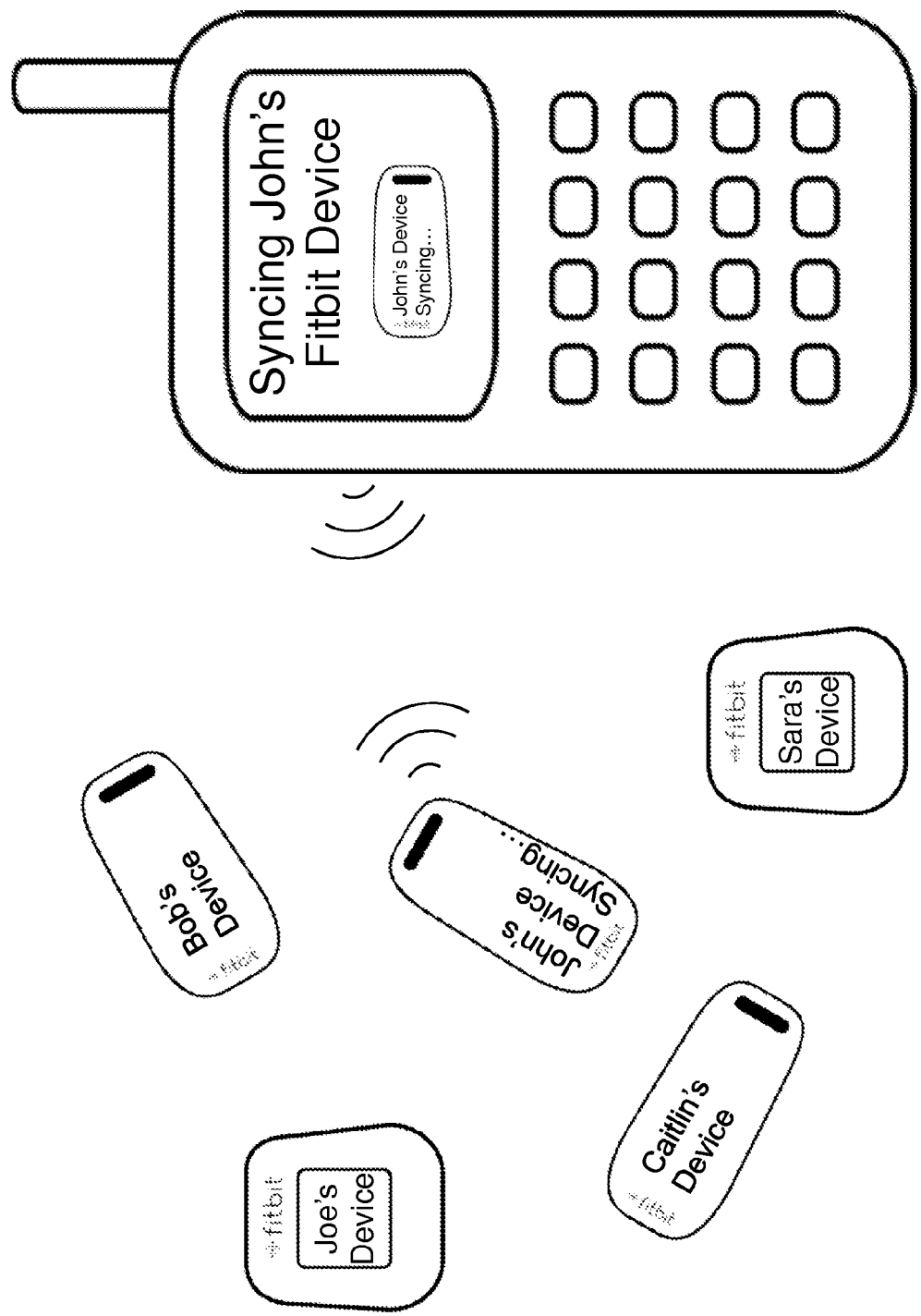
FIG. 4 shows an embodiment where a communication device syncs only the sensor device of a specific owner.

In another embodiment, a communication device might only sync if a specific sensor device is detected. In this instance, the communication device will listen for a wireless packet or sequence of wireless packets transmitted by a sensor device and analyze the packets to see if they contain the unique identifier of a specific sensor device and possibly the device type or user identifier of the owner of the sensor device. One such embodiment is illustrated in FIG. 4. The communication device may also only listen for the user identifier of the owner of the sensor device. When proper information is found in a wireless packet or sequence of wireless packets, unique-device syncing criteria is deemed to be met and the communication device starts and completes the syncing process in response. Other methods may be used to identify a unique device. In another embodiment, the type of device may be determined by an NFC tag integrated into the device or an RFID integrated into the device.

New Data Syncing Criteria

Figure 5:
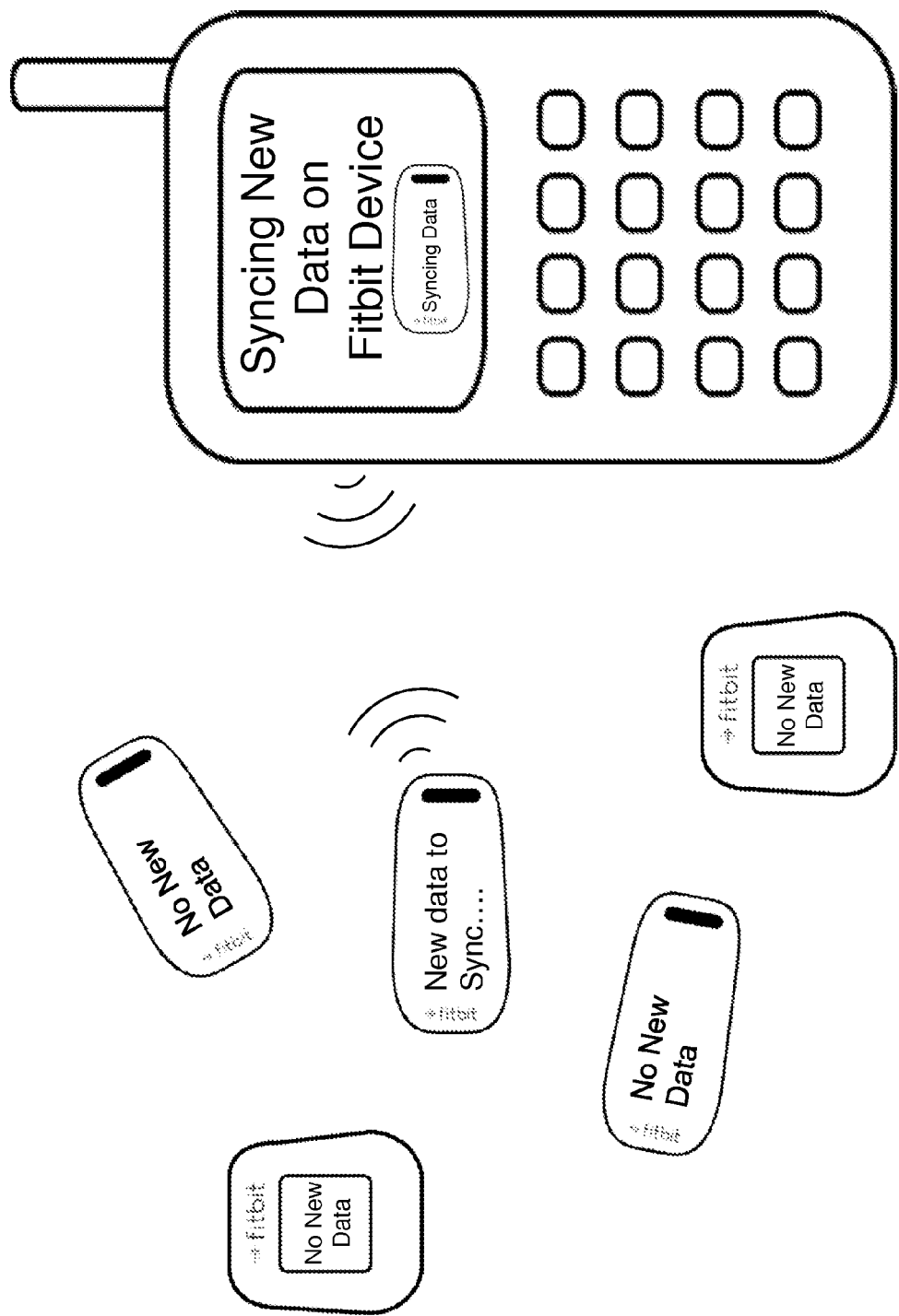
FIG. 5 shows an embodiment where a communication device syncs only with sensor devices which have new data.
Figure 6:
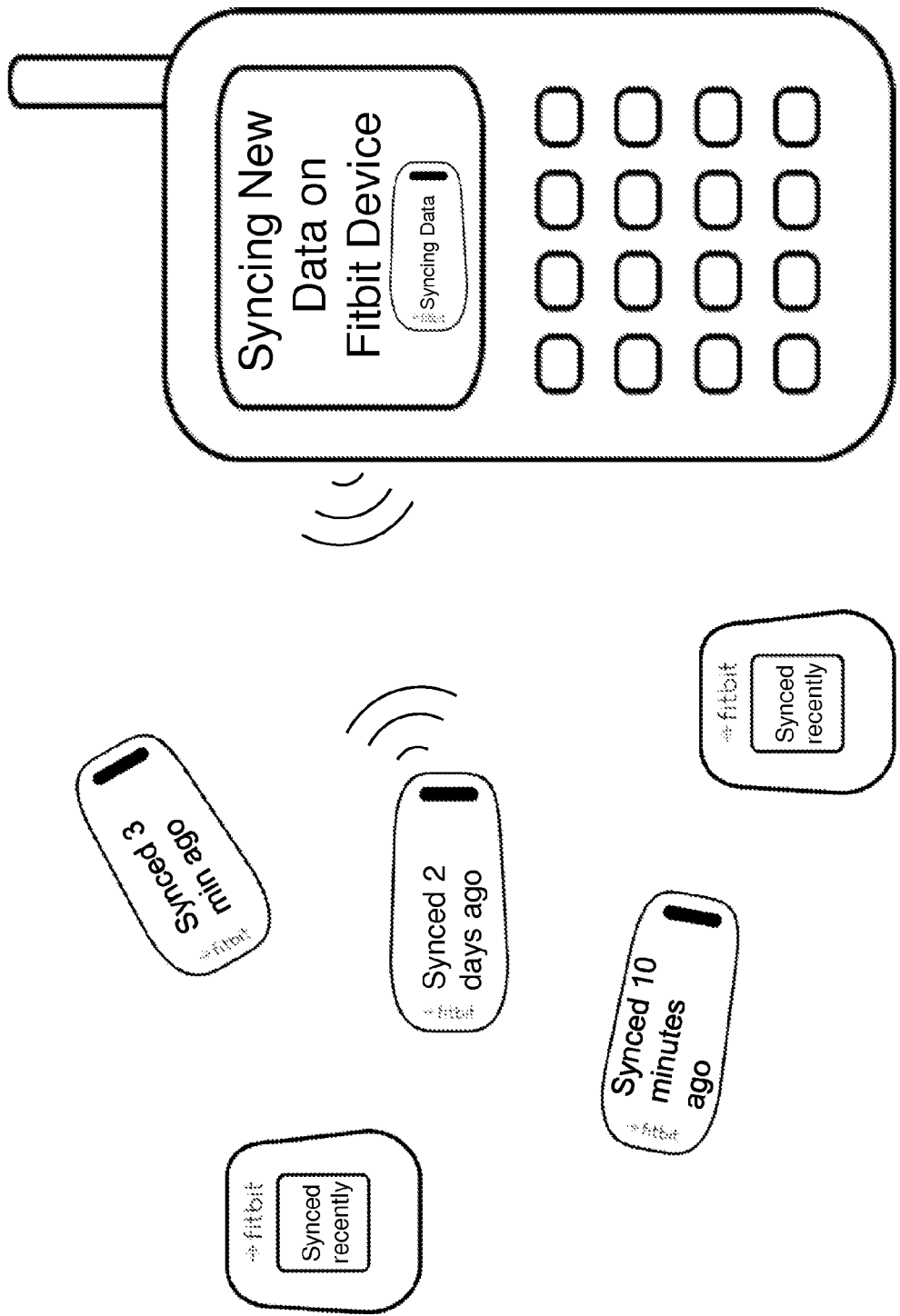
FIG. 6 shows an embodiment where a communication device syncs only with sensor devices which have not synced for a defined period of time, in this case, greater than 10 minutes ago.

In another embodiment, a communication device may be configured to sync only if a specific sensor device has a certain amount of new data to be synced as illustrated in FIG. 5 and FIG. 6. The sensor device might indicate this state, for example, if new data has been collected by the sensor device since the last time it synced with a communication device. In this instance, the communication device will listen for a wireless packet or sequence of packets transmitted by a sensor device and analyze them to see if they contain an indication that the sensor device wants or needs to sync. In some cases, a packet or packets might contain both the unique identifier of a device or device owner and an indication that the sensor device has new data that the sensor device wants to sync. In some other cases, the device might transmit a packet or packets that only contain the identifier of the device or owner and changes the device or owner identifier based on whether the sensor device has new data that the sensor device wants to sync. In either case, when such information is found in a wireless packet or sequence of wireless packets, a new-data syncing criteria is deemed to be met and the communication device starts and completes the syncing process in response.

The sensor device may determine whether it needs to sync or not based on information other than the acquisition of new data including but not limited to the charge state of the device, the operating mode of the device (e.g. battery saving or sleep mode), the state of the motion detector (e.g. whether the motion detector detects motion above a certain level or not), the state of other sensors such as heart rate, GSR, proximity, heat flux and temperature sensors. This other information may serve as a proxy for the acquisition of new data. For example, if the charge state of the sensor device is low, it is likely that the user has been acquiring new data with the device.

Goal-Based Data Syncing

The sensor device may determine whether or not it needs to sync based on goals of the user. The user may set these goals themselves or they may be set automatically. The sensor device could use the type of goal to determine when it should sync. For example, if the user has a goal based on the number of floors that they have climbed, the device may sync only when it detects that the user has climbed one or more floors. The criteria for meeting a goal may also be used by the device to determine when it should sync. For example, if a user's goal is to burn 2,000 calories, the device may try to sync when the user has reached 50%, 75%, and 100% of their goal. This would ensure that the user can see a reasonably precise measure of the progress to their goal on computing devices, portable communication devices, and/or web-based accounts associated with their device.

Physiological State Syncing Criteria

The device may determine whether or not it needs to sync based on the current or historical physiological state of the user. In one embodiment where the device can detect the sleep state of the user, the device may sync when the user wakes up. Alternatively, the device may sync immediately before or after the user wakes up. This would allow the user to see up to date data on their communication device or other server connected device immediately after waking up. In another embodiment, the device may sync if a user transitions from a sedentary to non-sedentary state or vice versa. For example, the device may sync when the user gets to work and when the user leaves work. In another embodiment, the device may sync not at the transition of one state to another, but while the user is in one state. For example, if the user has an elevated heart rate for a period greater than 10 minutes, the device may try to sync. This may enable a user to monitor their data during a run on their smartphone for example.

User Interaction Syncing Criteria

The sensor device may also sync based on when a user interacts with a communication device which displays synced data or data derived from synced data. In one embodiment, the server, communication device, sensor device or some combination of the three may determine, based on historical data when the user views synced data or information derived from synced data on their communication device. In one example, the device may sync to the user's communication device every time the user wakes up their communication device from sleep mode or turns on their communication device. This would allow the user to see the most up to date information when checking their data on the communication device. In another example, if a user always checks their smart phone at lunch time to see how many steps they walked that morning, the communication device may learn this habit and sync data immediately before the user's lunch time so that the most up to date step count is displayed. In another example, the user may always perform the same gesture or movement before checking their sensor device data. The communication may learn what gesture or motion is performed before the user checks their data and tell the device to sync whenever that gesture or motion is performed. In other cases, this gesture or motion sync criteria may be preprogrammed (not learned) to cause the sensor device to sync. For example, the sensor device may sync to a smart phone whenever the user reaches into their pocket to pull out their smartphone.

Activity Based Syncing

The sensor device may determine whether or not it needs to sync based on the activity of the user. In one embodiment, for example, the sensor device includes a motion sensor and may be configured (e.g., through a programmable setting) not to attempt to sync when the motion sensor detects that the user is active. This may allow the sensor device to reduce the power consumption due to failed or unnecessary syncing attempts. For example, if the user goes for a run with their device and they usually sync the device to a laptop, the device does not need to attempt a sync during the run as the user won't be using the laptop during the run. Conversely, the detection of motion may signal the device to sync in some cases. For example, if a user goes for a hike and they want to monitor their progress during the hike on a smart phone, the device may sync whenever the device detects motion which has a signature of hiking. Finally, in some cases a defined period of motion or lack thereof may be used to determine the syncing strategy. For example, the device may attempt to sync if it has detected motion for 15 minutes or longer.

In another embodiment, the user may interact with the device to indicate that the user is engaged in an activity. In some cases, the user may specify, as part of this interaction, the class or type of activity (e.g. walking, hiking, swimming, working out etc.) which is about to begin, in progress, or has recently ended. The sensor device may use these interactions (e.g., in the form of user input provided via any practicable user interface of the sensor device or a device communicatively coupled to the sensor device) to help determine an optimal or otherwise preferred time to sync. For example, the sensor device may sync at the beginning of a run (including prior to the run, for example, when the user provides input indicating an intent to begin a run) so that the client or server can notify friends that the user is running or planning to run to further encourage exercise. The sensor device may refrain from further sync attempts until it detects (or is notified through user interaction) that the user has completed the run.

Device or Owner Identifier Use as a Sync Flag

In a number of embodiments, the sensor device is capable of changing the device identifier and/or owner identifier based on the device's intent to sync, a particularly useful feature in cases where a mobile communication device listens for and initiates sync operations solely based on device or service unique identifiers. Typically, such a mobile communication device might initiate a sync whenever the sensor device came within range or stayed within range, thus potentially syncing more frequently than desirable and consuming undue power. By enabling the sensor device to dynamically change its device, service or owner identifier, however, and to set such identifier(s) to values recognized by the mobile communication device only when new data is available to sync, the mobile communication device would only initiate a sync when necessary, since the mobile communication device would only listen for identifiers that indicated that the sensor device needed to sync. This operation also enables the sensor device sync to co-exist and sync optimally with other communications devices that could base their decisions to sync on using more information contained in a sensor device's wireless packets.

Timestamp Syncing Criteria

In another instance, a communication device might attempt to sync with a sensor device only if a certain period of time has elapsed since the sensor device last synced with a communication device. In this instance, the communication device will listen for a wireless packet or sequence of packets transmitted by a sensor device and analyze them to see if they contain either a timestamp of the last sync time of the sensor device or an indicator of the elapsed time of the last sync (past minute, past 15 minutes, etc.). The communication device may decide based on the timestamp or elapsed time whether it wants to start and complete the syncing process.

Location Syncing Criteria

Figure 7:
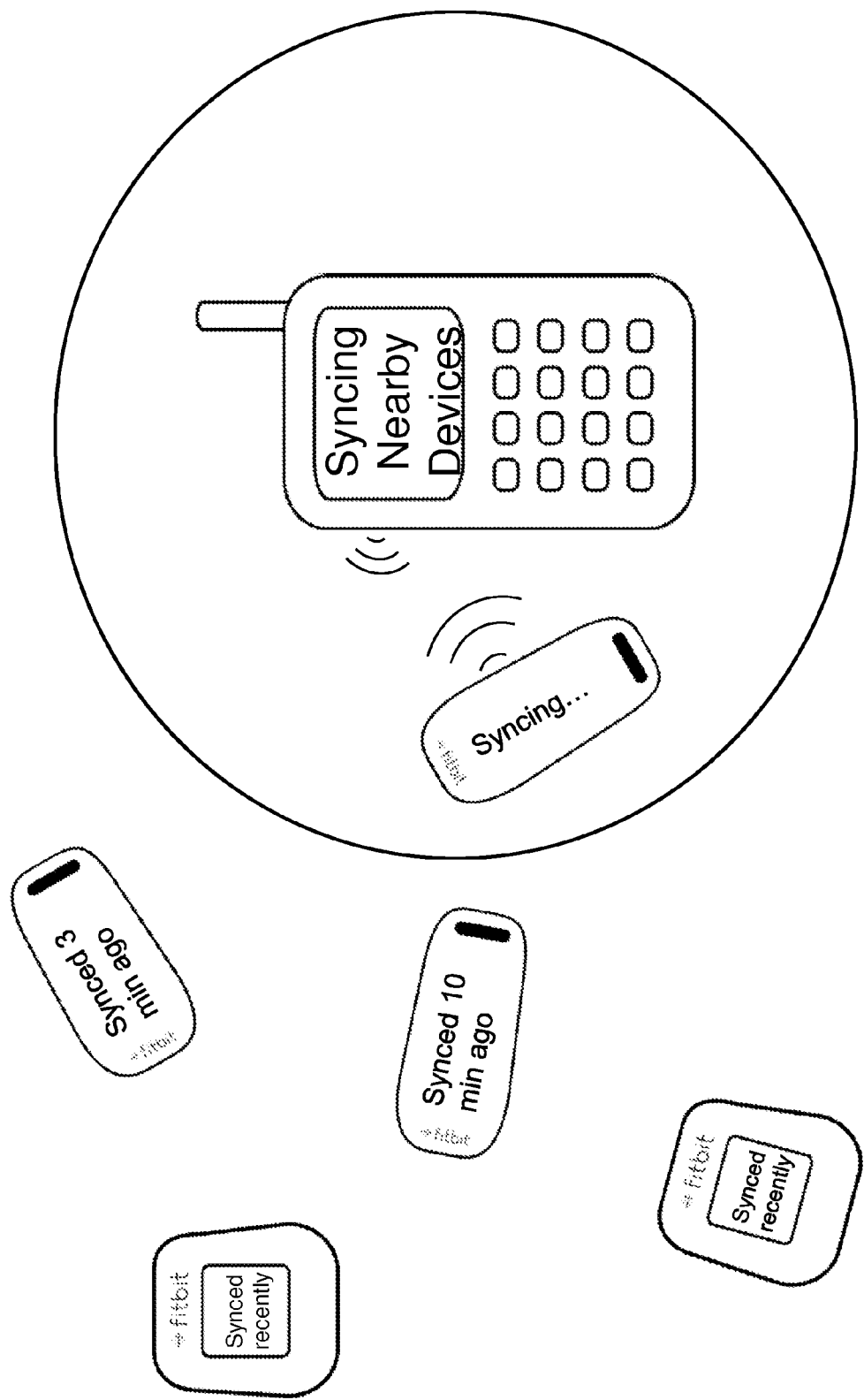
FIG. 7 shows an embodiment where a communication device syncs only with proximal sensor devices.
Figure 8:
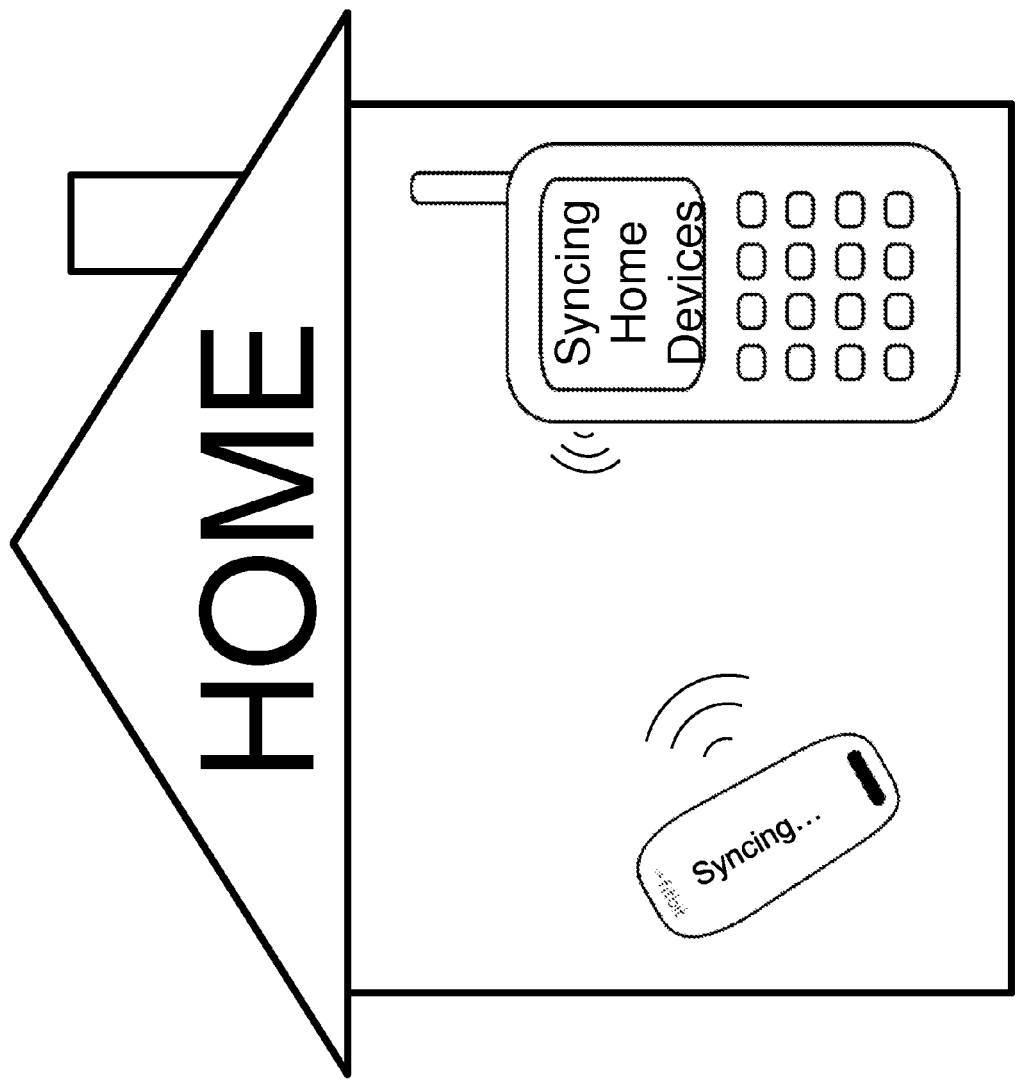
FIG. 8 shows an embodiment where a communication device syncs only with sensor devices located in a specific region, in this case a user's home.
Figure 8:
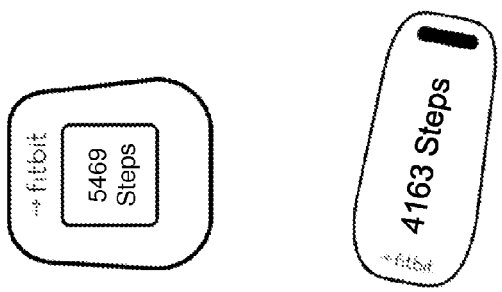

In another instance, a communication device might determine whether or not to sync a sensor device based on the absolute locations of the communication device and/or sensor device, and/or locations of the communication device and sensor device relative to one another. An illustration of this embodiment is shown in FIG. 7. Location of the communication device and/or sensor device may be determined through a plurality of means including but not limited to signal strength (e.g. RSSI) of a wireless signal such as, NFC, RFID, GPS, Wi-Fi, Zigbee, Ant+, Bluetooth, BTLE (Bluetooth Low Energy), or other radio network communication, optical detection through machine vision, audio signals, optical data transmission, or the spectral signature of a light source on the device. Sensor devices without built in GPS could be assumed to be in the same location as the client (e.g., communications device) syncing them; until heard from again they could be assumed to remain in the same place. In one embodiment, the location criteria for syncing may be the proximity of the sensor device to the communication device. In this case, the criteria is not based on the absolute location of either device, but instead, the relative locations of the communication and sensor devices. In another embodiment, the criteria for syncing may include the absolute position of the sensor device. For example, the communication device may allow any device to sync if they are in the user's home as seen in FIG. 8.

Data Connection Type Syncing Criteria

Figure 9:
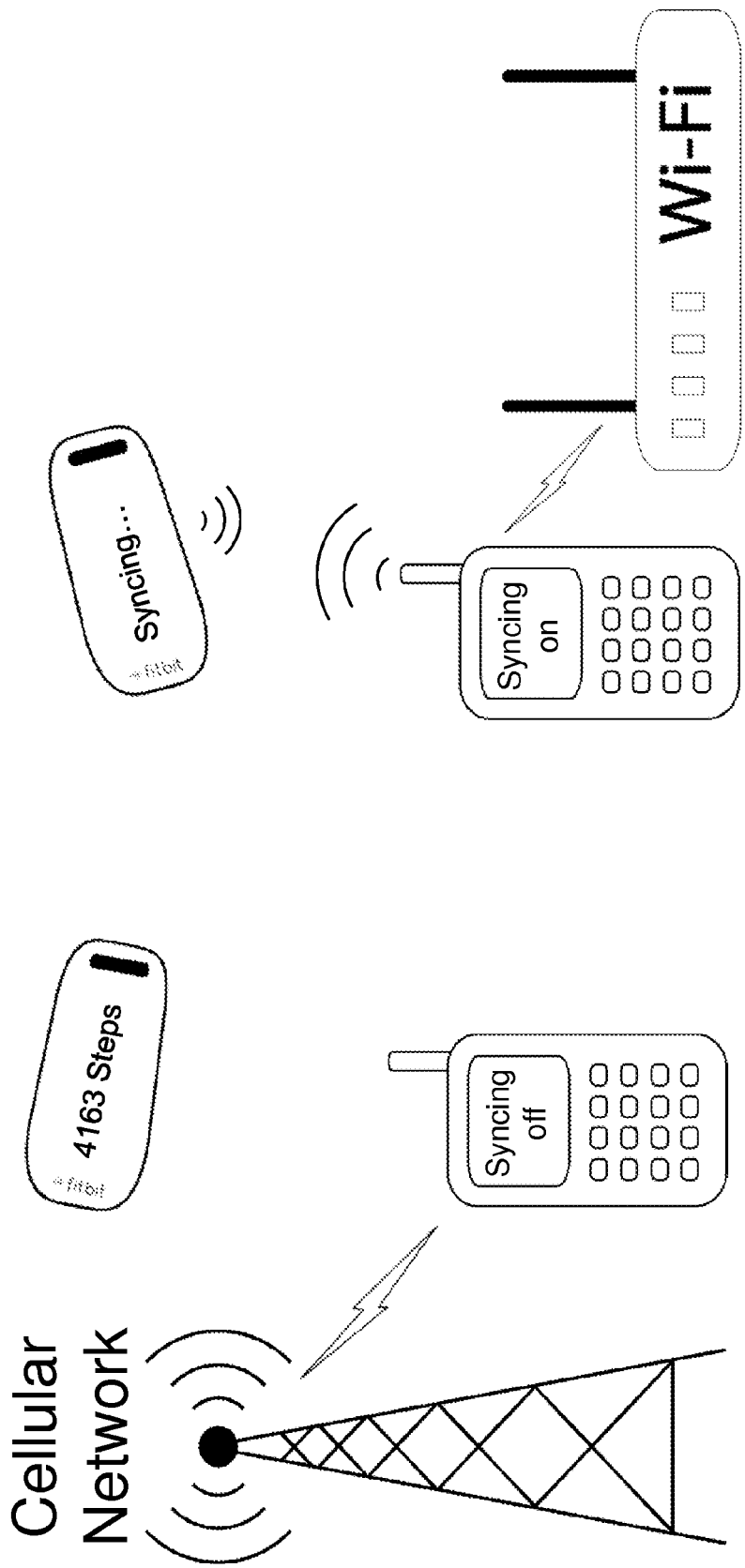
FIG. 9 shows an embodiment where a communication device syncs only with sensor devices when connected to a specific type of network, in this case Wi-Fi and not cellular.

The connection or set of connections that the communication device is connected to may be used as criteria for syncing and/or the type of syncing. For example, if the communication device is connected to a cellular network, the communication device may not sync any sensor devices so that the user minimizes their cellular network data usage (e.g. to avoid overage charges for example). When the communication device comes into contact with a Wi-Fi network, the communication device may then allow sensor devices to sync. In another embodiment, the type of sync may change depending on the network type that the communication device is connected to. This embodiment is illustrated in FIG. 9.

In another embodiment, the communication device may only sync high level data when it is connected to a cellular network. When connected to a Wi-Fi network the communication device may sync detailed data. In another embodiment, the communication device may sync data to local storage on the communication device when the communication device is not in contact with any networks. When the communication device comes into contact with a network, the communication device may then complete the upload of data to the server. Note that data connections other than Wi-Fi and cellular may be used in connection type syncing criteria including but not limited to other wireless networks such as NFC, RFID, GPS, Wi-Fi, Zigbee, Ant+, Bluetooth, BTLE and wired connections such as LAN and USB.

Multiple Syncing Criteria

More than one criteria for syncing may be met simultaneously or met within a certain time window of each other. Algorithms or programs for determining what action should be taken in such a case may reside on and be executed within the communication device, or a third party device in communication with the communication device such as a server. In one embodiment, each criterion for syncing or not syncing may be given a priority. For example, device identity criteria may have a higher priority than new data criteria so that no sync would occur for a sensor device not meeting the identity criteria, even if that sensor device has met the new data criteria. In practice, this may be useful when a user wants his or her personal sensor device to sync exclusively to the user's communication device (i.e., not to the communication device of another). Even if a sensor device is broadcasting its need to sync because it has new data, the user's communication device will decline to sync if the sensor device is not owned by the owner of the communication device.

In another embodiment, each or any of the above-described syncing criterion (or criteria) may be combined into meta-criteria; criteria which is only met when a set of sub-criteria are met. In one example a communication device might only sync if a sensor device has a specific identity and has new data that the sensor device wants to sync. The sensor device might indicate this state if there is new data collected by the sensor device since the last time it synced with a communication device. In this instance, the communication device will listen for a wireless packet or sequence of packets transmitted by a sensor device and analyze them to see if they contain an indication that the sensor device wants or needs to sync. In some cases, a packet or packets might contain both the unique identifier of a sensor device or identifier of the owner of the device and an indication that the sensor device has new data that it wants to sync. In some other cases, the device might transmit a packet or packets that only contain the identifier of the device or owner and change the device or owner identifier based on whether the sensor device has new data that it wants to sync. When proper information is found in a wireless packet or sequence of wireless packets, the communication device starts and completes the syncing process. Such a technique may be employed to allow a communication device to sync exclusively with the sensor device associated with the owner of the communication device at a time when this sensor device has new data to sync.

Note that meta-criteria and criteria that are met simultaneously or met within a certain time window of each other may have a prioritization structure similar to that discussed for criteria earlier in this disclosure.

Sensor Device Syncing Settings

The communications device may communicate with servers located on private networks or public networks such as the Internet. Through an interface located on a server or a communications device that may communicate with that server, a user may change settings, data or behavior on or of a sensor device, for example by providing instructions to program or otherwise load configuration data or settings into one or more configuration registers of the sensor device. These changes may include but are not limited to parameters for algorithms, time and alarm settings, personal biometric information (weight, height, age, gender, base metabolic rate, etc.), settings for the user interface (which UI screens to show, what information to show on each screen, the order of screens, etc.). Once a change is made, this change may be synced to a sensor device.

User Manipulation of Syncing Settings

The user of the communication device and/or sensor device may be able to change settings which determine how and when syncing occurs. The user may be able to change these settings on the sensor device (i.e., by providing input directly or indirectly that results in programming or loading of configuration values into one or more configuration registers of the sensor device), communication device, server, and or website in communication with one or more of the former. The user may be able to change or create the criterion, criteria, meta-criteria, and prioritize criteria and meta-criteria. In one embodiment, for example, a user may be able to set their phone to be a syncing hotspot or node for only their device or all devices. In another embodiment, the user may be able to combine criteria to create their own, more complex, criteria structure. For example, a user may allow their communication device to sync any device that has a location associated with their house when their communication device is in contact with Wi-Fi. The user may also choose to have their communication device always sync his or her own sensor device regardless of connection type and device location.

Server Initiated Syncing

In some cases, the server may determine when it is necessary for the sensor device to sync. In such a case, the communications device may gather a list of nearby sensor devices by listening for all wireless packets transmitted by nearby sensor devices for a period of time. The communications device may then query a server on private or public network to see if any of the sensor devices on the list have changes that needs to be synced. The server returns indication of which sensor devices have changes that need to be synced. The communication device then may automatically or upon direction by a user initiate syncing of the changes to the sensor devices in sequence or in parallel. Note that any of the criteria or meta-criteria disclosed herein may be aided or completed determined by the server instead of or in addition to the communication device and/or sensor device.

Syncing Security

Transmitted data may be encrypted when the communication device (one example of a client) is used as a tunnel between the sensor device and server. A secret key which enables decryption and encryption is shared between the device and server, but not the client. This prevents the client or an eavesdropping third party from being able to intercept and read the data. The encryption also allows any sensor device to sync to the server through any client without authentication, even if the client is untrusted, without fear of the client being able to read any of the transmitted data.

In some embodiments, it may be desirable for the client to be able to read data directly from the sensor device. For example, a user may have a smartphone application which permits data from the sensor device to be viewed. In order for the application to provide the user with a visualization of the data sent from the sensor device, the application should be able to read the data which is normally encrypted. Transferring data directly to the client instead of through the client to the server can also increase the speed with which data is transferred, allowing more immediate user interaction and visualization of data. Additionally, it may be desirable for the user to be able to sync, view and interact with data from the user's sensor device when the user's client is not connected to the server. For example, a user may want to sync his or her device to the user's smart phone (the communication device in this example) when the smart phone is out of range of any cellular network and not connected to the server.

Before sending data directly from the device to the client, it may first be determined that the client is a trusted entity. In order to trust the client, the server and/or device may perform an authentication of the client. In one embodiment, it may be undesirable to share the secret key (normally shared only with the device and the server) with the client. In order to authenticate the client without sharing the secret key, a secondary key may be generated using the main secret key, hereafter referred to as the derived key. This derived key may be generated by the server and sent to the client. The device may then use challenge-response authentication to determine if the client has a valid derived key. If this authentication is successful, the sensor device may then send unencrypted data to the client. Alternatively, the device and client may negotiate a session key after authentication of the client. Data would then be transferred encrypted between the device and client using the session key for encryption and decryption.

After being authenticated, the client may be given a token which allows the client to communicate directly with the sensor device without being authenticated again. This token may expire after a condition or set of conditions is met including but not limited to a certain number of data transfer sessions, a certain amount of data is transferred, and or after a certain period of time. The use of the token allows the client to transfer data from the sensor device without being connected to the server for authentication. This is useful in cases such as those already described where a user wants to sync a sensor device to a client (e.g. smart phone) which does not have connectivity to a remote server through a cellular network for example.

Although a specific security protocol is described herein, numerous variations of this protocol and/or alternative security protocols may be employed in connection with sensor device syncing. For example, instead of using a derived key, a key which is independent of the main secret key and known by both the server and the sensor device may be used. Additionally nonces may be used in one or more of the steps described in these protocols to help reduce the possibility of replay attacks.

Multiple Channel Syncing

The communication used between the sensor device and communication device, communication device and server, and/or communication device and server (directly) may make use of more than one channel. The use of more than one channel may enable further optimization of security, speed, and latency.

In one embodiment, the sensor device may have one communication channel with the communication device which is used to transfer data at high speed. The communication device may be considered a network sink in this case. A second communication channel may be formed with the communication device to transfer data to a server. This second communication channel uses the communication device as a network tunnel between the sensor device and server. A multichannel communication scheme may afford a variety of advantages such as having communication which may occur at multiple speeds and/or security levels. The communication channel between the sensor device and the communication device may be used to rapidly transfer high level data intended to be immediately displayed to the user. For example, in the case where the sensor device acts as a pedometer, the total number of steps that the user has taken in the day may be transferred through the high-speed channel. The second communication channel may be used to transfer more detailed data such as the log of steps taken each minute during the day to a server. The data may be encoded so that the communication device cannot parse it, adding a level of security to prevent the user or a third party from corrupting or manipulating the data with the communication device.

In another embodiment, a secondary communication channel may use a different wireless communication standard than the first communication channel. This secondary channel may be used to securely store or transmit data. In one embodiment, one channel may be used to transmit authentication data and a second channel using a different wireless standard may be used to transmit sensor data. For example, an NFC or RFID tag may transfer data that uniquely identifies the device. This tag may be write-protected so that the unique identity of the device is incorruptible.

Dynamic Communication Link Configuration

The configuration of the communication between the client and the device may be dynamically changed to optimize for highest data throughput and lowest energy usage. Changes to the low level communication parameters may occur after communication is established and while other communication over the connection is occurring. In one embodiment, it may be desirable for the client to determine how the communication link should be configured, but the client may not be able to configure all aspects of the communication link, namely the low level configurations. For example, in an implementation (or configuration) in which only the sensor device is able to configure certain aspects of the communication link, a special communication interface may be created to allow the client to communicate to the sensor device information needed to configure the communication link. In one embodiment, the type of communication used in dynamic communication link configuration may be Bluetooth or Bluetooth SMART.

Connection Oriented Syncing

In order to simplify the mechanism to accomplish syncing without using significant sensor and communication device power and to form a temporary strong relationship between sensor device and client where no other client may communicate with or interfere with the sensor device, a connection oriented approach may be employed. In one embodiment, the client connects to a sensor device, scales up communication speed, syncs, then remains connected but scales down communication speed so that the sensor device spends less energy than it normally would if it was wirelessly sending out packets at a higher communication speed. The client then listens for an indication on a specific sensor device data characteristic. When this indication is present, a message is sent to the communication device indicating that there is new data to sync. In one embodiment, the message may also inform the client of characteristics of the new data or even include the new data inline (i.e., as part of the message) if the volume of new data is small. If needed, the client scales up the communication link speed and performs a sync of all the data.

Another advantage of temporary client ownership of a sensor device communication link is that stateful transactions become possible. This enables the communication device to serve as not only a display for the sensor device but also an interactive terminal for it. In one embodiment, the user would like to change an alarm on the sensor device. The client could read the current state of alarms on the sensor device, hold the communication link open so that no one else may change the alarms, allow the user to edit the alarms on the client, and then finally write any alarm changes back to the sensor device.

Implementation of Sensor Device, Communication Device and Other Considerations

Figure 10:
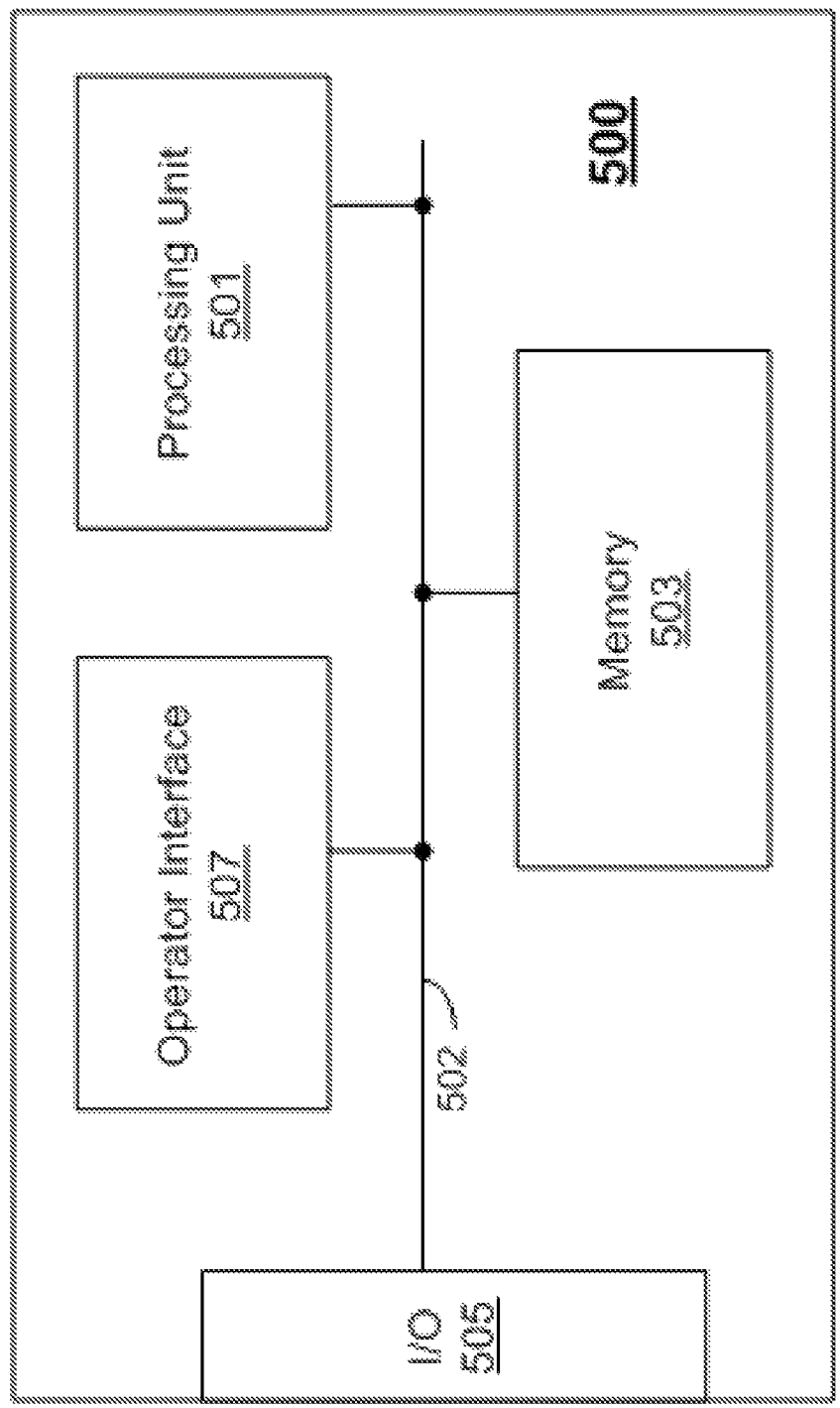
FIG. 10 shows a generalized embodiment of a computing device that may be used to implement a sensor device, communication device (or other client device), and/or server or other device in which the various operations described herein may be executed.
Figure 11:
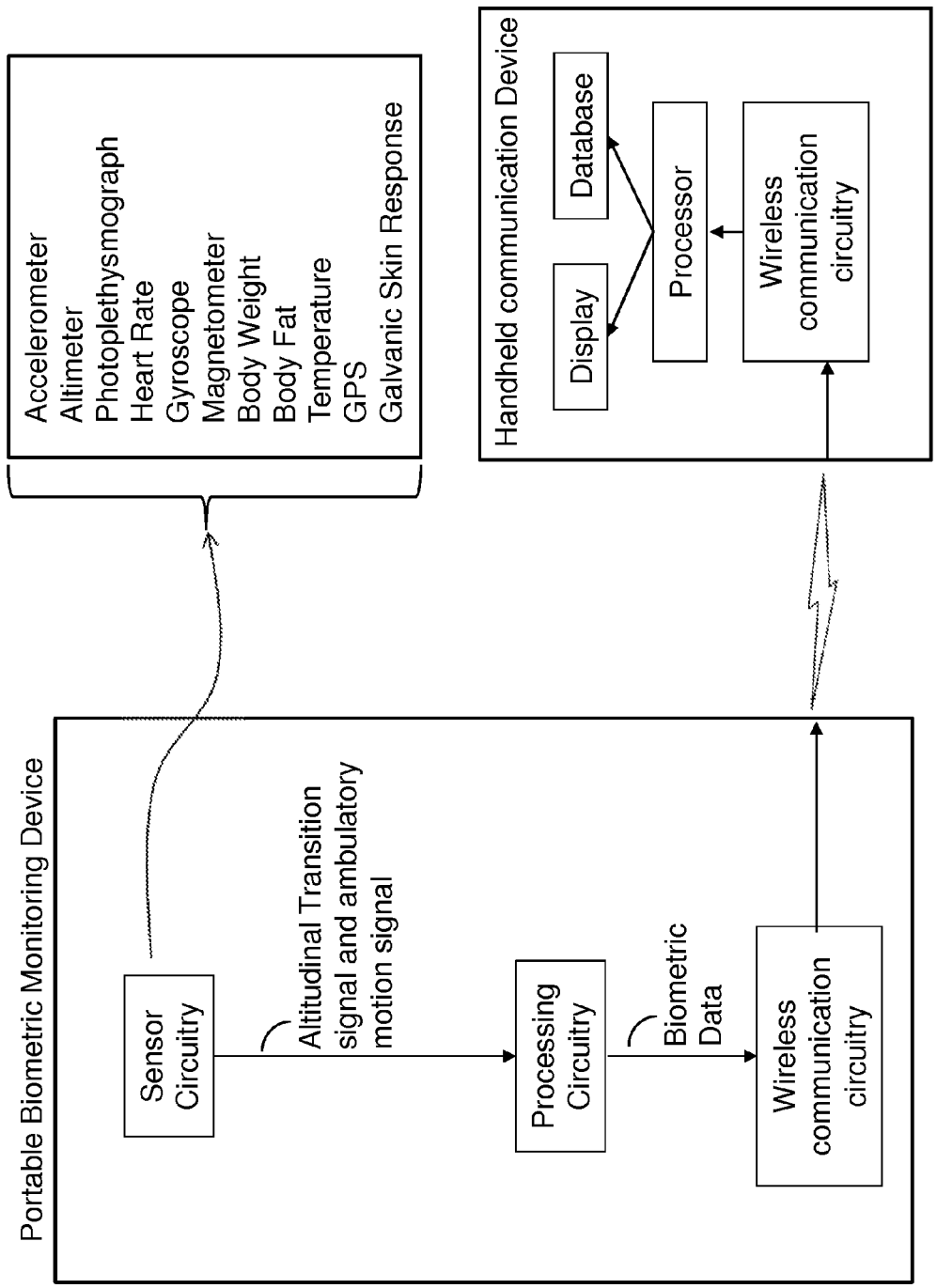
FIG. 11 shows an embodiment where altitudinal transition and or ambulatory motion signals acquired from sensor circuitry are operated on by processing circuitry to generate biometric data. This data is sent via wireless communication circuitry to a hand held communication device having wireless communication circuitry to receive the biometric data wirelessly.

FIG. 10 illustrates a generalized embodiment of a computing device 500 that may be used to implement a sensor device (client device), communication device, and/or server or other device in which the various operations described above may be executed (e.g., in a distributed manner between the sensor device and communication device). As shown, computing device 500 includes a processing unit 501, memory 503 for storing program code executed by the processing unit to effect the various methods and techniques of the above-described embodiments, and also to configuration data or other information for effecting various programmed or configuration settings in accordance with the embodiments described above. Note that the processing unit itself may be implemented by a general or special purpose processor (or set of processing cores) and thus may execute sequences of programmed instructions to effectuate the various operations associated with sensor device syncing, as well as interaction with a user, system operator or other system components.

Still referring to FIG. 10, computing device 500 further includes one or more input and/or output (I/O) ports 505 for receiving and outputting data (e.g., various wireless communications interfaces in accordance with communications standards described above), and a user interface 507 to present (display) and receive information to a human or artificial operator and thus enable an operator to control server-side and/or client-side inputs in connection with the above-described syncing operations. Though not shown, numerous other functional blocks may be provided within computing device 500 according to other functions it may be required to perform (e.g., one or more biometric sensors, environmental sensors, etc., within a sensor device, as well as one or more wireless telephony operations in a smartphone, and wireless network access in a mobile computing device, including a smartphone, tablet computer, laptop computer, etc.) and the computing device itself may be a component in a larger device, server or network of devices and/or servers. Further, the functional blocks within computing device 500 are depicted as being coupled by a communication path 502 which may include any number of shared or dedicated buses or signaling links. More generally, the functional blocks shown may be interconnected in a variety of different architectures and individually implemented by a variety of different underlying technologies and architectures. With regard to the memory architecture, for example, multiple different classes of storage may be provided within memory 503 to store different classes of data. For example, memory 503 may include non-volatile storage media such as fixed or removable magnetic, optical, or semiconductor-based recording media to store executable code and related data, volatile storage media such as static or dynamic RAM to store more transient information and other variable data.

The various methods and techniques disclosed herein may be implemented through execution of one or more a sequences of instructions (i.e., software program(s)) within processing unit 501, or by a custom-built hardware ASIC (application-specific integrated circuit), or programmed on a programmable hardware device such as an FPGA (field-programmable gate array), or any combination thereof within or external to processing unit 501.

Any of the various methodologies disclosed herein and/or user interfaces for configuring and managing same may be implemented by machine execution of one or more sequences instructions (including related data necessary for proper instruction execution). Such instructions may be recorded on one or more computer-readable media for later retrieval and execution within one or more processors of a special purpose or general purpose computer system or consumer electronic device or appliance, such as the system, device or appliance described in reference to FIG. 10. Computer-readable media in which such instructions and data may be embodied include, but are not limited to, non-volatile storage media in various forms (e.g., optical, magnetic or semiconductor storage media) and carrier waves that may be used to transfer such instructions and data through wireless, optical, or wired signaling media or any combination thereof. Examples of transfers of such instructions and data by carrier waves include, but are not limited to, transfers (uploads, downloads, e-mail, etc.) over the Internet and/or other computer networks via one or more data transfer protocols (e.g., HTTP, FTP, SMTP, etc.).

Various aspects and features of embodiments disclosed herein are set forth in the following numbered claims:

What is claimed is:

1. An activity monitoring device comprising:
a housing;
one or more components disposed in the housing, the one or more components including one or more sensors configured to capture activity monitoring data;
a memory device for storing the activity monitoring data;
a wireless communications circuit; and
a processor coupled to the wireless communications circuit, the memory device, and the one or more components, the processor configured to:
access, from the memory device, information identifying a first state of a first component of the one or more components;
determine whether the first state identified by the accessed information satisfies a threshold condition for synchronizing the activity monitoring data; and
in response to a determination that the first state satisfies a threshold condition for synchronizing the activity monitoring data, initiate synchronizing of the activity monitoring data with a computing device, the synchronizing causing sending of the activity monitoring data from the memory device to the computing device via the wireless communications circuit.

2. The activity monitoring device of claim 1, wherein the first state includes a charge state of the activity monitoring device.

3. The activity monitoring device of claim 2, wherein the first component includes a battery, wherein the charge state of the activity monitoring device includes a level of power stored within the battery, wherein the threshold condition is satisfied based on a change in the level of power.

4. The activity monitoring device of claim 1, wherein the first state includes an operating mode of the activity monitoring device, wherein the operating mode includes a battery saving mode or a sleep mode.

5. The activity monitoring device of claim 1, wherein the first state includes an activity level of the activity monitoring data, wherein the threshold condition is satisfied based on one of (i) the activity level of the activity monitoring data being greater than a pre-determined level and (ii) the activity level of the activity monitoring data being less than a pre-determined level.

6. The activity monitoring device of claim 1, wherein the one or more sensors include a first sensor and a second sensor, the first component including the first sensor, wherein the first state includes a state of the first sensor, wherein the processor is further configured to, in response to a determination that the state of the first sensor satisfies the threshold condition, initiate synchronizing of the activity monitoring data captured by the second sensor with the computing device.

7. The activity monitoring device of claim 1, wherein the one or more sensors include at least one of a motion sensor, an altitude sensor, a heart rate sensor, or a body temperature sensor.

8. The activity monitoring device of claim 1, wherein the first state is indicative of an amount of the activity monitoring data accumulated since a most recent synchronization, wherein the threshold condition is satisfied based on the amount of new data exceeding a threshold amount of the activity monitoring data.

9. An activity monitoring device comprising:
a housing;
one or more components disposed in the housing, the one or more components including one or more sensors configured to capture activity monitoring data;
a memory device for storing the activity monitoring data;
a wireless communications circuit; and
a processor coupled to the one or more components, the memory device, and the wireless communications circuit, the processor configured to:
access the activity monitoring data from the memory device, the activity monitoring data indicative of an amount of activity performed by a user of the activity monitoring device or a value of a physiological metric of the user;
determine whether the amount of activity or the value of the physiological metric satisfies a threshold condition for synchronizing the activity monitoring data, the threshold condition comprising a predefined goal for the amount of activity or the value of the physiological metric; and
in response to a determination that the amount of activity or the value of the physiological metric satisfies the threshold condition for synchronizing the activity monitoring data, initiate synchronizing of the activity monitoring data with a computing device the synchronizing causing sending of the activity monitoring data from the memory device to the computing device via the wireless communications circuit.

10. The activity monitoring device of claim 9, wherein the predefined goal includes at least one of a number of floors to climb, a number of calories to burn, a number of steps to complete, an amount of weight to loose, an amount of time asleep, or a body fat value.

11. The activity monitoring device of claim 9, wherein the predefined goal is a predefined portion of another predefined goal.

12. The activity monitoring device of claim 9, wherein the one or more sensors include at least one of a motion sensor, an altitude sensor, a heart rate sensor, or a body temperature sensor.

13. The activity monitoring device of claim 9, wherein the predefined goal is specified based on user input to an electronic device via a user interface of the electronic device, the electronic device being configured to communicate with the activity monitoring device or the computing device via a wireless network.

14. An activity monitoring device comprising:
a housing;
one or more components disposed in the housing, the one or more components including one or more sensors configured to capture activity monitoring data for identifying an activity performed;
a memory device for storing the activity monitoring data;
a wireless communications circuit; and
a processor coupled to the one or more components, the memory device, and the wireless communications circuit, the processor configured to:
access the activity monitoring data from the memory device;
determine whether a state of a physiological metric generated from the activity monitoring data satisfies a threshold condition for synchronizing the activity monitoring data; and
in response to a determination that the state of the physiological metric satisfies the threshold condition for synchronizing the activity monitoring data initiate synchronizing of the activity monitoring data with a computing device, the synchronizing causing sending of the activity monitoring data from the memory device to the computing device via the wireless communications circuit.

15. The activity monitoring device of claim 14, wherein the state of the physiological metric is indicative of a type of the activity performed, wherein the processor is further configured to determine, based on the type of the activity, whether the threshold condition is satisfied.

16. The activity monitoring device of claim 14, wherein the state of the physiological metric is indicative of whether a user of the activity monitoring device is in a sleep state or an awake state, wherein the processor is further configured to determine, based on whether the user is in the sleep state or the awake state, whether the threshold condition is satisfied.

17. The activity monitoring device of claim 14, wherein the state of the physiological metric is indicative of whether a user of the activity monitoring device is in a sedentary state or a non-sedentary state, wherein the processor is further configured to determine, based on whether the user is in the sedentary state or the non-sedentary state, whether the threshold condition is satisfied.

18. The activity monitoring device of claim 14, wherein the state of the physiological metric is indicative of whether a user of the activity monitoring device is arriving at a specific location, wherein the processor is further configured to determine, based on whether the user is arriving at the specific location, whether the threshold condition is satisfied.

19. The activity monitoring device of claim 14, wherein the processor is further configured to initiate synchronizing of the activity monitoring data with the computing device in response to a determination that the state of the physiological metric satisfies the threshold condition for an amount of time greater than a pre-determined amount of time.

20. The activity monitoring device of claim 19, wherein the processor is further configured to determine that the state of the physiological metric satisfies the threshold condition based on at least one of a change in a heart rate, a change in a number of steps taken, or a change in motion.

21. The activity monitoring device of claim 14, wherein the one or more sensors include at least one of a motion sensor, an altitude sensor, a heart rate sensor, or a body temperature sensor.

22. The activity monitoring device of claim 14, wherein the physiological metric includes a number of calories and the activity monitoring data includes a body weight value.

23. The activity monitoring device of claim 14, wherein the activity monitoring device is configured to be worn on a body of a user and the computing device is configured to be carried by the user.

24. The activity monitoring device of claim 14, wherein the processor is further configured to refrain from initiating synchronizing of the activity monitoring data based on the state of the physiological metric indicating an active state.

25. The activity monitoring device of claim 24, wherein the state of the physiological metric indicates the active state when the activity identified based on the activity monitoring data comprises a running activity.

26. The activity monitoring device of claim 14, wherein the processor is further configured to refrain from initiating synchronizing of the activity monitoring data based on the state of the physiological metric indicating a lack-of-motion state, and to initiate synchronizing of the activity monitoring data based on the state of the physiological metric indicating a state of motion.

27. An activity monitoring device comprising:
a housing;
one or more components disposed in the housing, the one or more components including one or more sensors configured to capture activity monitoring data;
a memory device for storing the activity monitoring data;
a wireless communications circuit; and
a processor coupled to the one or more components, the memory device, and the wireless communications circuit, the processor configured to:
access the activity monitoring data from the memory device;
determine whether the activity monitoring data is indicative of a predetermined motion for synchronizing the activity monitoring data;
in response to a determination that the activity monitoring data is indicative of the predetermined motion for synchronizing the activity monitoring data, initiate synchronizing of the activity monitoring data with a computing device, the synchronizing causing sending of the activity monitoring data from the memory device to the computing device via the wireless communications circuit.

28. The activity monitoring device of claim 27, wherein the predetermined motion comprises a predetermined activity determined to be performed by a user of the activity monitoring device.

29. The activity monitoring device of claim 27, wherein the processor is further configured to refrain from synchronizing the activity monitoring data in response to a determination that the activity monitoring data is not indicative of the predetermined motion.

30. The activity monitoring device of claim 27, wherein the processor is further configured to initiate synchronizing of the activity monitoring data based on whether a timestamp associated with the predetermined motion indicated by the activity, monitoring data.

* * * * *